United States Patent
Hall et al.

(10) Patent No.: US 11,384,058 B2
(45) Date of Patent: Jul. 12, 2022

(54) METHOD FOR THE SYNTHESIS OF 3-R-1,4,2-DIOXAZOL-5-ONES

(71) Applicant: Tesla Motors Canada ULC, North York (CA)

(72) Inventors: David S. Hall, Halifax (CA); Jeffery Raymond Dahn, Halifax (CA); Toren Hynes, Oyster Pond (CA)

(73) Assignees: PANASONIC HOLDINGS CORPORATION, Osaka (JP); TESLA, INC., Austin, TX (US)

( * ) Notice: Subject to any disclaimer, the term of this patent is extended or adjusted under 35 U.S.C. 154(b) by 0 days.

(21) Appl. No.: 16/440,584

(22) Filed: Jun. 13, 2019

(65) Prior Publication Data
US 2020/0392091 A1 Dec. 17, 2020

(51) Int. Cl.
| | | |
|---|---|---|
| *A61P 35/00* | (2006.01) | |
| *A61P 37/00* | (2006.01) | |
| *C07D 519/00* | (2006.01) | |
| *C07D 487/04* | (2006.01) | |
| *C07D 487/14* | (2006.01) | |
| *C07D 471/14* | (2006.01) | |
| *C07D 273/01* | (2006.01) | |
| *C07D 413/04* | (2006.01) | |

(52) U.S. Cl.
CPC ......... *C07D 273/01* (2013.01); *C07D 413/04* (2013.01)

(58) Field of Classification Search
CPC ........ A61P 35/00; A61P 37/00; C07D 273/01; C07D 413/04; C07D 519/00; C07D 487/04; C07D 487/14; C07D 471/14
See application file for complete search history.

(56) References Cited

PUBLICATIONS

Dube-et-al., 2009, 11(24), 5622-2625.*
Alder et al., 2016, Updating and further expanding GSK's solvent sustainability guide, Green Chem., 198:3879-3890.
Chen et al., 2017, Rhodium(III)-catalyzed directed C-H amidation of N-nitrosoanilines and subsequent formation of 1,2-disubstituted benzimidazoles, Chem. Asian J., 12:2804-2808.
Defoin et al., 1991, From 1-(silyloxy)butadiene to 4-amino-4-deoxy-DL-erythrose and to 1-amino-1-deoxy-DL-erythritol derivatives via hetero-Diels-Alder reactions with acylnitroso dienophiles, Helvetica Chimica Acta, 74:1653-1670.
Ding et al., 2018, Experimental and computational studies on $H_2O$-promoted, Rh-catalyzed transient-ligand-free ortho-C($sp^2$)-H amidation of benzaldehydes with dioxazolones, Chem. Commun., 54:8889-8892.
Dolomanov et al., 2009, OLEX2; a complete structure solution, refinement and analysis program, J. Applied Cryst., 42:339-341.
Dube et al., 2009 Carbonyldiimidazole-mediated Lassen rearrangement, Organic Letters, 11(24):5622-5625.
Farrugia, 2012, WinGX and ORTEP for Windows: an update, Journal of Applied Crystallography, 45:849-854.
Fulmer et al., 2010, NMR chemical shifts of trace impurities; common laboratory solvents, organics, and gases in deuterated solvents relevant to the organometallic chemist, Organometallics, 29:2176-2179.
Hall et al., 2018, Dioxazolone and nitrile sulfite electrolyte additives for lithium-ion cells, Journal of the Electrochemical Society, 165(13):A2961-A2967.
Halskov et al., 2017, Synthesis of [5,6]-bicylic heterocycles with a ring-junction nitrogen atom: rhodium(III)-catalyzed C-H functionalization of alkenyl azoles, Angew. Chem., 129:9311-9315.
Hande, 2017, Ru(II)-catalyzed C-H amidation of indoline at the C7-position using dioxazolone as an amidating agent: synthesis of 7-amino indoline scaffold, J. Org. Chem., 82:13405-13413.
Hoang et al., 2018, Synthesis of azolo[1,3,5]triazines via rhodium(III)-catalyzed annulation of N-azolo imines and dioxazolones, J. Org. Chem. 83:9522-9529.
Huang et al., 2017, Microwave-assisted Cp*Co$^{III}$-catalyzed C-H activation/double C-N bond formation reactions to thiadiazine 1-oxides, Org. Lett., 19:1128-1131.
Hynes et al., A one-pot method for the synthesis of 3-(hetero-)aryl-1,4,2-dioxazol-5-ones, www.nrcresearchpress.com, downloaded on Jan. 11, 2020, 24 pp.
Jiang et al., 2017, Iminyl-radicals by oxidation of α-imino-oxy acids: photoredox-neutral alkene carboimination for the synthesis of pyrrolines, Angew. Chem. Int. Ed., 56:12273-12276.
Knecht et al., 2019, Intermolecular, branch-selective, and redox-neutral Cp*Ir$^{III}$-catalyzed allycic C-H amidation, Angew. Chem. Int. Ed., 58:7117-7121.
Li et al., 2012, Prop-1-ene-1,3-sultone as SEI formation additive in propylene carbonate-based electrolyte for lithium ion batters, Electrochemistry Communications, 17:92-95.
Liu et al., 2018, Cp*Co(III)-catalyzed amidation of olefinic and aryl C-H bonds: highly selective synthesis of enamides and pyrimidones, Chem. Commun, 54:4354-4348.
Mishra et al., 2018, Ir(III)/MPAA-catalyzed mild and selective C-H amidation of N-sulfonyl ketimines: access to benzosultam-fused quinazolines/quinazolinones, J. Org. Chem., 83:3756-3767.
Park et al., 2015, Mechanistic Studies on the Rh(III)-mediated amido transfer process leading to robust C-H amination with a new type of amidating reagent, J. Am. Chem. Soc., 137:4534-4542.
Park et al., 2015, Study of sustainability and scalability in the Cp*Rh(III)-catalyzed direct C-H amidation with 1,4,2-dioxazol-5-ones, Org. Process Res. Dev., 19:1024-1029.
Roser et al., 2017, Highly effective solid electrolyte interphase-forming electrolyte additive enabling high voltage lithium-ion batteries, Chem. Mater., 29:7733-7739.
Sheldrick, 2015, Crystal structure refinement with Shelxl, Acta Cryst., C71:3-8.
Schlosser et al., Feb. 2015, Human health effects of dichloromethane: key findings and scientific issues, Environmental Health Perspectives, 123(2):114-119.
Sheldrick, 2014, SHELXT: integrating space group determination and structure solution, Acta Cryst., A70:C1437.
Shi et al., 2017, Co(III)-catalyzed enaminone-directed C-H amidation for quinolone synthesis, Org. Lett. 19:2418-2421.

(Continued)

*Primary Examiner* — Sun Jae Yoo
(74) *Attorney, Agent, or Firm* — Knobbe, Martens, Olson & Bear, LLP

(57) ABSTRACT

Provided are methods of preparing 3-R-1,4,2-dioxazol-5-one compounds using convenient and efficient methods. Also provided are 3-R-1,4,2-dioxazol-5-one compounds produced using the methods described.

15 Claims, 33 Drawing Sheets

(56) References Cited

PUBLICATIONS

Tan et al., 2017 Thioamide-directed cobalt (III)-catalyzed selective amidation of C(sp$^3$)-H bonds, Angew. Chem. Int. Ed., 56:16550-16554.

Wang et al., 2018, Cp*Co(III)-catalyzed ortho C-H amidation of 2-pyridinyl ferrocenes with 1,4,2-diozazol-5-ones, Journal of Catalysis, 361:393-397.

Wang et al., 2018, Rh-catalyzed transient directing group promoted C-H amidation of benzaldehydes utilizing dioxazolones, Chin. J. Chem., 36:213-216.

Wrodnigg et al., 1999. Ethylene sulfite as electrolyte additive for lithium-ion cells with graphitic anodes, Journal of the Electrochemical Society, 146(2):470-472.

Wu et al., 2018, Rh-catalyzed annulation of ortho-C-H bonds of 2-arylmidazoles with 1,4,2-dioxazol-5-ones toward 5-arylimidazo[1,2-c]quinazolines, Adv. Synth, Catal., 360:1111-1115.

Yao et al., Jul. 2010, Effect of ethylene sulfate as electrolyte additive on performance of Li-ion batteries, Chinese Journal of Applied Chemistry, 27(7), 6 pp.(abstract).

Zhou et al., 2018, CuH-catalyzed asymmetric hydroamidation of vinylarenes, Angew. Chem. Int. Ed., 57:6672-6675.

* cited by examiner 3-phenyl-1,4,2-dioxazol-5-one

¹H 3-(2-thiophene)-1,4,2-dioxazol-5-one

¹H 3-(2-thiophene)-1,4,2-dioxazol-5-one $^{13}$C 3-(p-fluorophenyl)-1,4,2-dioxazol-5-one $^{13}$C 3-(m-fluorophenyl)-1,4,2-dioxazol-5-one

¹H 3-(m-fluorophenyl)-1,4,2-dioxazol-5-one $^{13}C$ 3-(m-fluorophenyl)-1,4,2-dioxazol-5-one $^{19}$F 3-(o-fluorophenyl)-1,4,2-dioxazol-5-one

¹H 3-(o-fluorophenyl)-1,4,2-dioxazol-5-one 3-(*p*-methoxyphenyl)-1,4,2-dioxazol-5-one

¹H 3-(*p*-methoxyphenyl)-1,4,2-dioxazol-5-one

¹³C 3-(p-nitrophenyl)-1,4,2-dioxazol-5-one

¹H 3-(p-nitrophenyl)-1,4,2-dioxazol-5-one $^{13}C$ 3-(m-nitrophenyl)-1,4,2-dioxazol-5-one

¹H 3-(m-nitrophenyl)-1,4,2-dioxazol-5-one $^{13}C$ 3-(o-nitrophenyl)-1,4,2-dioxazol-5-one

¹H

3-(o-nitrophenyl)-1,4,2-dioxazol-5-one
$^{13}$C 3,3'-(1,4-phenylene)bis-1,4,2-dioxazol-5-one

¹H

3-(p-chlorophenyl)-1,4,2-dioxazol-5-one
$^1$H

3-(p-chlorophenyl)-1,4,2-dioxazol-5-one
$^{13}$C 3-(m-chlorophenyl)-1,4,2-dioxazol-5-one

¹H 3-(o-chlorophenyl)-1,4,2-dioxoazol-5-one $^{13}$C

METHOD FOR THE SYNTHESIS OF 3-R-1,4,2-DIOXAZOL-5-ONES

TECHNICAL FIELD

The present disclosure relates to preparation of 3-R-1,4,2-dioxazol-5-one compounds. In particular, the present disclosure relates to a more convenient method for the preparation of 3-R-1,4,2-dioxazol-5-one compounds than was previously known or utilized.

BACKGROUND

In recent years, 3-R-1,4,2-dioxazol-5-one compounds have been found to be versatile reagents, especially for regioselective amidation at the ortho C—H position of aromatic moieties. These reagents act via the formation of N-acyl nitrene intermediates and are most often used with electron-poor aromatic substrates, such as those with ketone, aldehyde, 2-phenylpyridine, nitrosoaniline, arylimidazole, 2-pyridinyl ferrocenes, and indoline substituents. They are finding increasingly diverse applications, including the amidation of N-sulfonyl ketimines, thiadiazine-1-oxides, and thioamides. Alkenyl azoles can be functionalized, and the Lossen rearrangement can be used to efficiently prepare isocyanates, allowing a more environmentally-friendly alternative for the Hoffmann and the Curtius rearrangements. Together with N-azolo imines and a Rh(III) catalyst, they can be used to make azolo[1,3,5]triazines, common motifs used in drug design, for enantioselective hydroamination of vinyl arenes with a copper hydride catalyst, to amidate olefin or aryl C—H bonds to make enamides and pyrimidones, which can also act as a directing group for a second C—H amidation, and for the ortho-imidation of substituted imadazopyridines. Recently, 3-methyl-1,4,2-dioxazol-5-one found a completely new use as an electrolyte additive for improving the performance of lithium-ion cells. Even more recently, the closely related 3-phenyl-1,4,2-dixoazol-5-one was similarly tested as an electrolyte additive and was shown to significantly extend the lifetime of lithium-ion cells during prolonged cycling.

To further increase the use of dioxazolone compounds, robust methods are needed that can be used to prepare them with a wide range of functional group substitutions. Historically, these compounds have been prepared by combining a hydroxamic acid with N,N'-carbonyldiimidazole ("CDI") in dichloromethane as shown below in Reaction I.

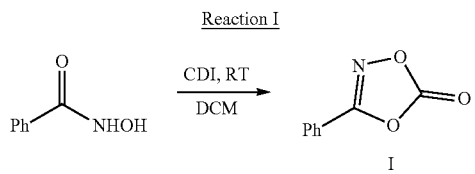

Reaction I

Reaction I shows the historically used route for the synthesis of 3-phenyl-1,4,2-dioxazol-5-one from benzohydroxamic acid and N,N'-carbonyldiimidazole.

Occasionally, acetonitrile or ethyl acetate has been used as the solvent instead. While this method generally provides products with high purities and high yields, many hydroxamic acids are not commercially available, limiting the range of compounds that easily can be prepared by this route. Furthermore, many of the existing methods involve the use of dichloromethane, a relatively hazardous and environmentally harmful solvent that is not favored by some industrial chemical producers. While hydroxamic acids can be easily prepared via the reaction of acyl chlorides with hydroxylamine hydrochloride in a biphasic system of water and diethyl ether, using sodium carbonate as a base, the hydroxamic acids are often difficult to isolate from the reaction mixture, and the scope of this reaction is limited by the use of water, which means the hydroxamic acids must be thoroughly dried so as to not hydrolyze the CDI used for formation of the 1,4,2-dixoazol-5-ones.

The reaction route used to date for production of 3-R-1,4,2-dioxazol-5-one compounds is time consuming, inefficient, and expensive and there is a need for improvement to the methods for production of these compounds. In the present disclosure, presented is a more simplified approach to synthesizing 3-aryl-substituted-1,4,2-dixoazol-5-ones using a "one-pot" method that employs inexpensive, commercially available aryl acyl chlorides, hydroxylamine hydrochloride, and CDI. The reaction proceeds readily under mild conditions and requires no expensive catalysts to proceed.

SUMMARY

According to certain embodiments, provided is a method of preparing 3-R-1,4,2-dioxazol-5-one compounds. The method includes the steps of: combining hydroxylamine hydrochloride, triethylamine, and a first organic solvent to prepare a reaction mixture; dissolving a R-substituted acyl chloride in a second organic solvent to prepare a R-substituted acyl chloride solution; dissolving triethylamine in a third organic solvent to prepare a triethylamine solution; adding the R-substituted acyl chloride solution and the triethylamine solution to the reaction mixture over a first predetermined time period; stirring the resulting reaction mixture for a second predetermined amount of time; adding CDI to the reaction mixture; stirring the resulting reaction mixture for a third predetermined amount of time; adding acid to quench the reaction; and obtaining a 3-R-1,4,2-dioxazol-5-one compound. In some embodiments, the R-substituted acyl chloride is selected from benzoyl chloride, 2-thiophenecarbonyl chloride, p-toluoyl chloride, 2-naphthoyl chloride, p-fluorobenzoyl chloride, m-fluorobenzoyl chloride, o-fluorobenzoyl chloride, p-methoxybenzoyl chloride, p-nitrobenzoyl chloride, m-nitrobenzoyl chloride, o-nitrobenzoyl chloride, p-teraphthaloyl chloride, p-chlorobenzoyl chloride, m-chlorobenzoyl chloride, or o-chlorobenzoyl chloride.

In yet further embodiments, the first organic solvent is N,N-dimethylformamide. In some embodiments, the second organic solvent is ethyl acetate or tetrahydrofuran. In other embodiments, the third organic solvent is ethyl acetate or tetrahydrofuran. The second and third organic solvents may be the same or different.

In some embodiments, the first predetermined amount of time is ten or more minutes. In yet further embodiments, the first predetermined amount of times is between about ten and thirty minutes, between about ten minutes and two hours, is about ten minutes, about twenty minutes, about thirty minutes, or is more than twenty minutes, or more than thirty minutes. In other embodiments, the first predetermined amount of time is less than about two hours. In further embodiments, the second predetermined amount of time is one or more hours. In yet further embodiments, the second predetermined amount of time is about one hour, about ninety minutes, about two hours, or between about one hour and six hours. In yet further embodiments, the second predetermined amount of time is less than six hours. In yet further embodiments, the third predetermined amount of time is twenty or more minutes. In yet further embodiments, the third predetermined amount of time is between about twenty minutes and about one hour, between about twenty minutes and about two hours is about twenty minutes, about thirty minutes, about one hour, or about two hours. In yet further embodiments, the third predetermined amount of time is less than two hours.

In yet further embodiments, the 3-R-1,4,2-dioxazol-5-one compound has a purity of at least 50%, 55%, 60%, 65%, 70%, 75%, or greater. In other embodiments, the method further includes the step of purifying the 3-R-1,4,2-dioxazol-5-one compound to a purity of at least 75%, 80%, 85%, 90%, 95%, or greater.

In other embodiments of method, the method is performed at ambient temperature and pressure. In further embodiments of the method, the reaction mixture is cooled to 0° C. before the R-substituted acyl chloride solution and the triethylamine solution are added to the reaction mixture.

In yet further embodiments of the method, the 3-R-1,4,2-dioxazol-5-one compound is selected from 3-phenyl-1,4,2-dioxazol-5-one, 3-thiophene-1,4,2-dioxazol-5-one, 3-tolyl-1,4,2-dioxazol-5-one, 3-(2-naphthyl)-1,4,2-dioxazol-5-one, 3-(p-fluorophenyl)-1,4,2-dioxazol-5-one, 3-(m-fluorophenyl)-1,4,2-dioxazol-5-one, 3-(o-fluorophenyl)-1,4,2-dioxazol-5-one, 3-(p-methoxyphenyl)-1,4,2-dioxazol-5-one, 3-(p-nitrophenyl)-1,4,2-dioxazol-5-one, 3-(m-nitrophenyl)-1,4,2-dioxazol-5-one, 3-(o-nitrophenyl)-1,4,2-dioxazol-5-one, 3,3'-(1,4-phenylene)-bis-1,4,2-dioxazol-5-one, 3-(p-chlorophenyl)-1,4,2-dioxazol-5-one, 3-(m-chlorophenyl)-1,4,2-dioxazol-5-one, or 3-(o-chlorophenyl)-1,4,2-dioxazol-5-one.

According to other embodiments provided herein, provided are 3-R-1,4,2-dioxazol-5-one compounds prepared by the methods described herein. In some embodiments, the compound is selected from -phenyl-1,4,2-dioxazol-5-one, 3-thiophene-1,4,2-dioxazol-5-one, 3-tolyl-1,4,2-dioxazol-5-one, 3-(2-naphthyl)-1,4,2-dioxazol-5-one, 3-(p-fluorophenyl)-1,4,2-dioxazol-5-one, 3-(m-fluorophenyl)-1,4,2-dioxazol-5-one, 3-(o-fluorophenyl)-1,4,2-dioxazol-5-one, 3-(p-methoxyphenyl)-1,4,2-dioxazol-5-one, 3-(p-nitrophenyl)-1,4,2-dioxazol-5-one, 3-(m-nitrophenyl)-1,4,2-dioxazol-5-one, 3-(o-nitrophenyl)-1,4,2-dioxazol-5-one, 3,3'-(1,4-phenylene)-bis-1,4,2-dioxazol-5-one, 3-(p-chlorophenyl)-1,4,2-dioxazol-5-one, 3-(m-chlorophenyl)-1,4,2-dioxazol-5-one, or 3-(o-chlorophenyl)-1,4,2-dioxazol-5-one. In yet further embodiments, the compound is 3-methyl-1,4,2-dioxazol-5-one or 3-phenyl-1,4,2-dixoazol-5-one.

In yet further embodiments, the 3-R-1,4,2-dioxazol-5-one compound has a purity of at least 50%, 55%, 60%, 65%, 70%, 75%, 80%, 85%, 90%, 95%, or greater.

DETAILED DESCRIPTION OF THE DISCLOSURE

Figure 1:
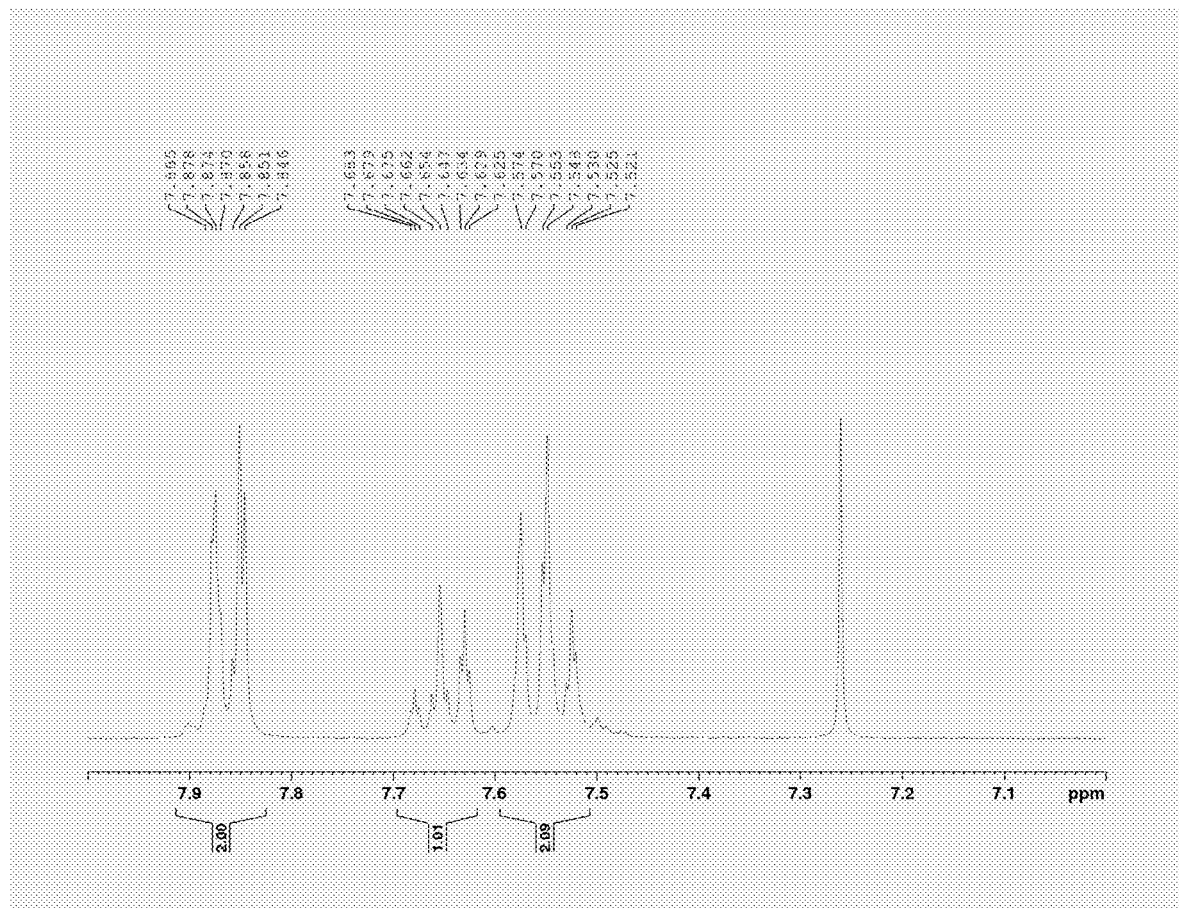
FIG. 1 is the $^1$H NMR (CDCl$_3$, 300 MHz) spectrum for 3-phenyl-1,4,2-dioxazol-5-one prepared in accordance with an embodiment as described herein.

The following description is presented to enable any person skilled in the art to make and use the embodiments, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present inventions are not limited to the embodiments shown, but are to be accorded the widest scope consistent with the principles and features disclosed herein.

Again, 3-R-1,4,2-dioxazol-5-ones are a class of compounds that are increasingly finding diverse uses, including as regioselective amidation reagents and as electrolyte additives that enable long cycling lifetimes in rechargeable lithium-ion batteries. Conventional methods for their synthesis tend to be slow and time-consuming, requiring isolation and thorough drying of a hydroxamic acid intermediate, followed by a separate cyclization step with CDI. Furthermore, the cyclization is typically performed in dichloromethane, an environmentally harmful solvent.

This disclosure provides a new "one-pot" method for the synthesis of these compounds. The phrase "one-pot" method means that the method eliminates the need for isolation of the intermediate. Additionally, according to embodiments described herein, certain methods allow for production of 3-R-1,4,2-dioxazol-5-ones without the use of halogenated solvents. In embodiments described herein, the reaction is performed using mainly environmentally benign ethyl acetate and a relatively small amount of N,N-dimethylformamide. According to certain embodiments described herein, the reaction proceeds readily at room temperature and requires no expensive metal catalysts to function.

A need was identified to prepare a wider range of 3-R-1,4,2-dioxazol-5-one compounds for testing as lithium-ion battery electrolyte additives. The thiophene-substituted compound was deemed particularly interesting, based on a number of S-containing heterocyclic additives that were previously reported to improve battery performance and lifetime. However, a commercial supplier of 2-thiophene hydroxamic acid could not be located and a 2-thiophenecarbonyl chloride was used instead to prepare 2-thiophene hydroxamic acid in-house, according to Reaction II.

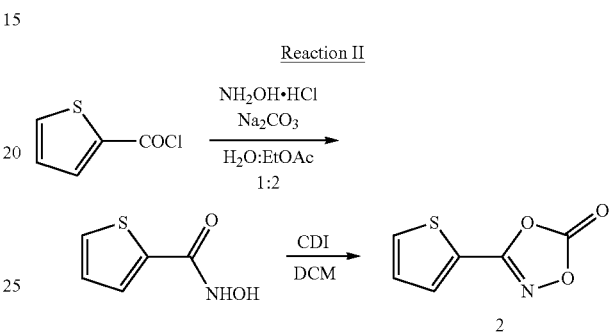

Reaction II

The hydroxamic acid was then isolated and used to synthesize 3-(2-thiophene)-1,4,2-dioxazol-5-one using the conventional Reaction I, giving an overall yield of 61%.

However, this synthetic route was unsatisfactory for a few reasons: i) it generated a significant amount of halogenated solvent waste; ii) it provided a relatively low overall yield, and iii) it was time-consuming to isolate the intermediate reagent only to immediately use it in a subsequent reaction. For these reasons, and given the increasing demand for these compounds in a variety of chemical applications, a goal was established to develop a "one-pot" method that generates and uses the hydroxamic acid intermediate without the need for isolation in the overall method of producing 3-R-1,4,2-dioxazol-5-one compounds. As described herein, the presently described methods have surprisingly discovered favorable solvent combinations and reaction parameters that provide acceptable yields of 3-R-1,4,2-dioxazol-5-one compounds and do not require timely and inefficient intermediate reagent isolation.

EXPERIMENTS

Identification of Solvents p-Toluoyl chloride is less expensive and more representative of other substituents than the thiophene-substituted acyl chloride. Therefore, a method was developed using p-toluoyl chloride as the starting reagent, with the objective of preparing 3-(p-tolyl)-1,4,2-dioxazol-5-one, shown as (3) in Table 2.

The first challenge was identifying a solvent in which the acyl chloride, the hydroxylamine hydrochloride, and the CDI are all soluble. It was determined that hydroxylamine hydrochloride is insoluble in pure DCM, THF, and EtOAc (Table 1). Therefore none of these are suitable for use as the reaction medium in the "one-pot" methods as described herein. All three reagents may be dissolved in chloroform and, when tested, the product was observed by $^1H$ and $^{13}C$ NMR. However, after 1 h of reflux, the reaction yield remained modest (63%) and the purity was unsatisfactory.

The need for post-synthetic purification, the relatively low reaction yield, the use of a toxic halogenated solvent, and the use of energy intensive reflux make this route undesirable. Finally, N,N-dimethylformamide (DMF) was tested as a solvent but gave very low reaction yield (22%).

TABLE 1

Solvent systems tested in this work and the corresponding yields for the synthesis of 3-(p-tolyl)-1,4,2-dioxazol-5-one from p-toluoyl chloride, hydroxylamine hydrochloride, and CDI.

| Solvent 1 | Solvent 2 | Ratio (v/v) | Yield | Notes |
| --- | --- | --- | --- | --- |
| Dichloromethane | — | — | 0% | Hydroxylamine not soluble in solvent |
| Tetrahydrofuran | — | — | 0% | Hydroxylamine not soluble in solvent |
| Chloroform | — | — | 63% | Product very impure, chloroform refluxed for 1 h |
| DMF | DCM | 1:2 | 39% | DCM added following formation of hydroxamic acid |
| DMF | — | — | 22% | |
| EtOAc | — | — | 0% | Hydroxylamine not soluble in solvent |
| EtOAC | DMF | 5:1 | 77% | Deprotonation of hydroxylamine carried out in pure DMF, then EtOAc was added |

Next, the reaction was repeated in DMF and DCM was added immediately before the addition of the CDI. This was observed to nearly double the reaction yield, but it was nonetheless quite low (39%). Finally, a 1:5 blend by volume of DMF and EtOAc was tested, where the hydroxylamine was deprotonated in pure DMF before the addition of the co-solvent. This gave a significantly higher yield than any of the other solvent systems (77%). Moreover, it used only a small amount of the environmentally unfriendly DMF, while eliminating the use of halogenated solvents completely. When the synthesis of 3-(2-thiophene)-1,4,2-dioxazol-5-one was repeated using this solvent blend and the one-pot method, the yield was significantly increased, relative to the prior art two-step method discussed above (76% cf. 61%).

Preparation of 3-R-1,4,2-dioxazol-5-ones from Hydroxamic Acids

Benzohydroxamic acid (21 g, 153 mmol, 1 eq) was dissolved in 600 mL of ethyl acetate, and N,N'-carbonyldiimidazole (30 g, 185 mmol, 1.2 eq) was added in one portion. The reaction was stirred at room temperature for 30 min, then 2 M HCl (250 mL) was added. The reaction was extracted 3× with ethyl acetate (100 mL) then dried over $Na_2SO_4$. The solvent was removed under reduced pressure to afford 16.6 g of 3-phenyl-1,4,2-dioxazol-5-one (shown as (1) in Table 2) as a white crystalline solid (66%).

One-Pot Method—Testing Scale

Reaction III

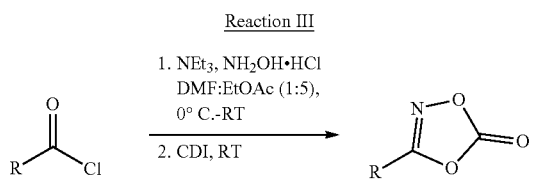

Reaction III: General scheme of reaction conditions used to prepare the 3-R-1,4,2-dioxazol-5-ones. R=aryl.

Hydroxylamine hydrochloride (13.2 mmol, 0.90 g, 1.1 eq), was dissolved in N,N-dimethylformamide (DMF, 20 mL) at room temperature in a 250 mL three-necked round-bottomed flask equipped with a magnetic stir bar. Triethylamine (13.2 mmol, 1.8 mL, 1.1 eq) was added in one portion. The solution was stirred for 5 minutes, then ethyl acetate (70 mL) was added to the solution, and the reaction mixture was cooled to 0° C. R-substituted acyl chloride (12.0 mmol, 1 eq) was dissolved in 20 mL of ethyl acetate and placed into an addition funnel. Triethylamine (1.8 mL, 13.2 mmol, 1.1 eq) was dissolved in another 20 mL of ethyl acetate and placed into a separate dropper funnel. Both funnels were placed onto the 250 mL three necked round-bottomed flask and the contents were added dropwise to the reaction mixture over the course of 15 minutes. The reaction was allowed to gradually warm up to room temperature.

For the synthesis reaction involving terapthaloyl chloride, the quantities of hydroxylamine hydrochloride, triethylamine, and CDI were doubled, to account for the presence of two acyl chloride functional groups. The method, including solvent volumes, was otherwise unaltered.

After stirring for an additional five hours, N,N'-carbonyldiimidazole (CDI, 12.0 mmol, 1.95 g, 1 eq) was added in one portion to the reaction mixture containing the triethylamine and the hydroxamic acid. The reaction was allowed to proceed for another 30 minutes at room temperature. Solid white triethylamine hydrochloride ($Et_3NHCl$) was removed from the reaction mixture by suction filtration. The reaction solution was then quenched with 75 mL of 1M $H_2SO_{4(aq)}$, extracted with ethyl acetate (2×45 mL), and dried over anhydrous $Na_2SO_4$. The ethyl acetate was evaporated under reduced pressure leaving the protonated reaction product dissolved in DMF. Leaving the solution under vacuum for a sufficient time allows the ethyl acetate to be completely removed before proceeding. 10% aqueous $NaHCO_3$ was added to the remaining liquid to precipitate the product, which was collected by suction filtration.

Testing of Various Acyl Chlorides

The one-pot synthesis was then tested with a wide variety of aromatic acyl chlorides. Starting from benzoyl chloride, the one-pot synthesis gave high yield (81%) and purity of the target compound (3-phenyl-1,4,2-dioxazol-5-one, shown as (1) in Table 2). In addition to benzoyl chloride itself, electron-rich benzoyl chlorides, such as p-methoxybenzoyl chloride (used to prepare 3-(p-methoxy)-1,4,2-dioxazol-5-one, shown as (8) in Table 2), were successful. Electron-poor benzoyl chlorides, such as p-nitrobenzoyl chloride (used to prepare 3-(p-nitrophenyl)-1,4,2-dioxazol-5-one, shown as (9) in Table 2), also formed product in good yield, especially when the nitro group was in the para position. Lower yield was observed with m-nitrobenzoyl chloride (used to prepare 3-(m-nitrophenyl)-1,4,2-dioxazol-5-one, shown as (10) in Table 2). o-nitrobenzoyl chloride (used to prepare 3-(o-nitrophenyl)-1,4,2-dioxazol-5-one, shown as (11) in Table 2), however, gave a poor yield, possibly because of steric interactions between the dioxazolone and the nitro group. In addition to 2-thiophenecarbonyl chloride, discussed above to prepare 3-(2-thiophene)-1,4,2-dioxazol-5-one, shown as (2) in Table 2, this procedure is also able to tolerate 2-naphthoyl chloride (used to prepare 3-(2-naphthyl)-1,4,2-dioxazol-5-one, shown as (4) in Table 2). The reaction tolerated monofluorinated benzoyl chlorides (used to prepare 3-(p-fluorophenyl)-1,4,2-dioxazol-5-one, 3-(m-fluorophenyl)-1,4,2-dioxazol-5-one, and 3-(o-fluorophenyl)-1,4,2-dioxazol-5-one, shown as (5), (6), (7), respectively, in Table 2), regardless of the substitution pattern, as well as monochlorinated benzoyl chlorides (used to prepare 3-(p-chlorophenyl)-1,4,2-dioxazol-5-one, 3-(m-chlorophenyl)-1,4,2-dioxazol-5-one, and 3-(o-chlorophenyl)-1,4,2-dioxazol-5-one, shown as (13), (14), (15), respectively, in Table 2), although the yields were modest for the ortho and para isomers. Interestingly, this is the reverse of the trend observed for the benzoyl fluorides, where the ortho-fluorophenyl compound (used to prepare 3-(o-fluorophenyl)-1,4,2-dioxazol-5-one, shown as (7) in Table 2) had the greatest yield. Generally, the introduction of fluorine moieties is known to affect compound solubility. It is therefore possible that the lower yields of the para- and meta-substituted aryl fluorides (e.g., those used to prepare 3-(p-fluorophenyl)-1,4,2-dioxazol-5-one, 3-(m-fluorophenyl)-1,4,2-dioxazol-5-one, respectively) are attributable to lower solubility in the ethyl acetate used for extractions. Finally, it was considered whether the reaction would tolerate a reagent with more than one acyl chloride group. It was found that the reaction tolerates p-teraphthaloyl chloride (used to produce 3, 3'-(1,4-phenylene) bis-1,4,2-dioxazol-5-one, shown as (12) in Table 2).

Nuclear Magnetic Resonance (NMR) Spectroscopy

Solution NMR spectroscopy characterized the following compounds produced according to the method described above. NMR spectra were recorded on either a Bruker 300 MHz or a Bruker 500 MHz NMR spectrometer controlled by TopSpin software. Chemical shifts are reported in ppm referenced to the residual solvent peaks ($^1$H NMR) or the deuterated solvent ($^{13}$C NMR).

TABLE 2

Structures and yields of the products prepared via the one-pot method.

| | |
|---|---|
| 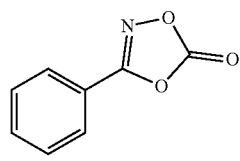 (81%) | 1 |
| 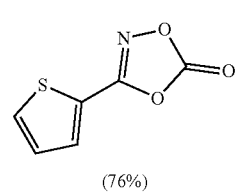 [SMILES: O=c1onc(-c2cccs2)o1] (76%) | 2 |

TABLE 2-continued

Structures and yields of the products prepared via the one-pot method.

| | |
|---|---|
| 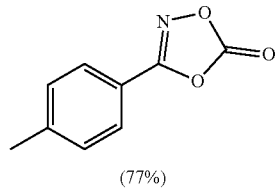 (77%) | 3 |
| 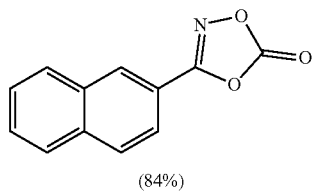 [SMILES: O=c1onc(-c2ccc3ccccc3c2)o1] (84%) | 4 |
| 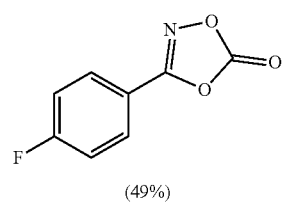 [SMILES: O=c1onc(-c2ccc(F)cc2)o1] (49%) | 5 |
| 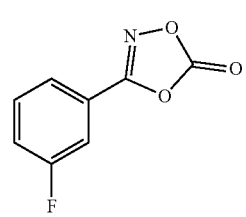 (51%) | 6 |
| 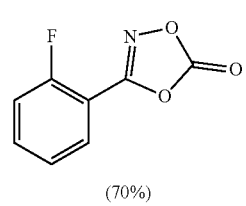 [SMILES: O=c1onc(-c2ccccc2F)o1] (70%) | 7 |
| 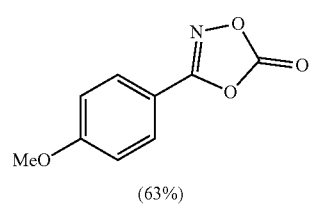 [SMILES: COc1ccc(-c2noc(=O)o2)cc1] (63%) | 8 |
| 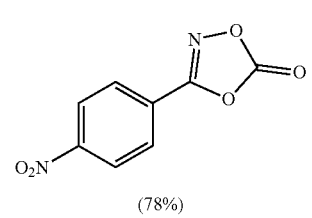 [SMILES: O=c1onc(-c2ccc([N+](=O)[O-])cc2)o1] (78%) | 9 |

TABLE 2-continued

Structures and yields of the products prepared via the one-pot method.

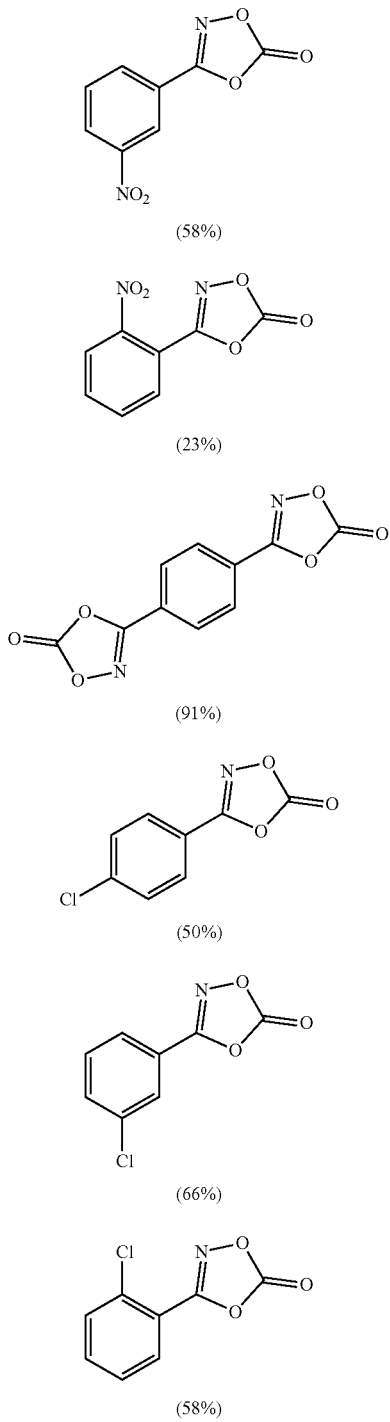

| | |
|---|---|
| (58%) | 10 |
| (23%) | 11 |
| (91%) | 12 |
| (50%) | 13 |
| (66%) | 14 |
| (58%) | 15 |

Figure 2:
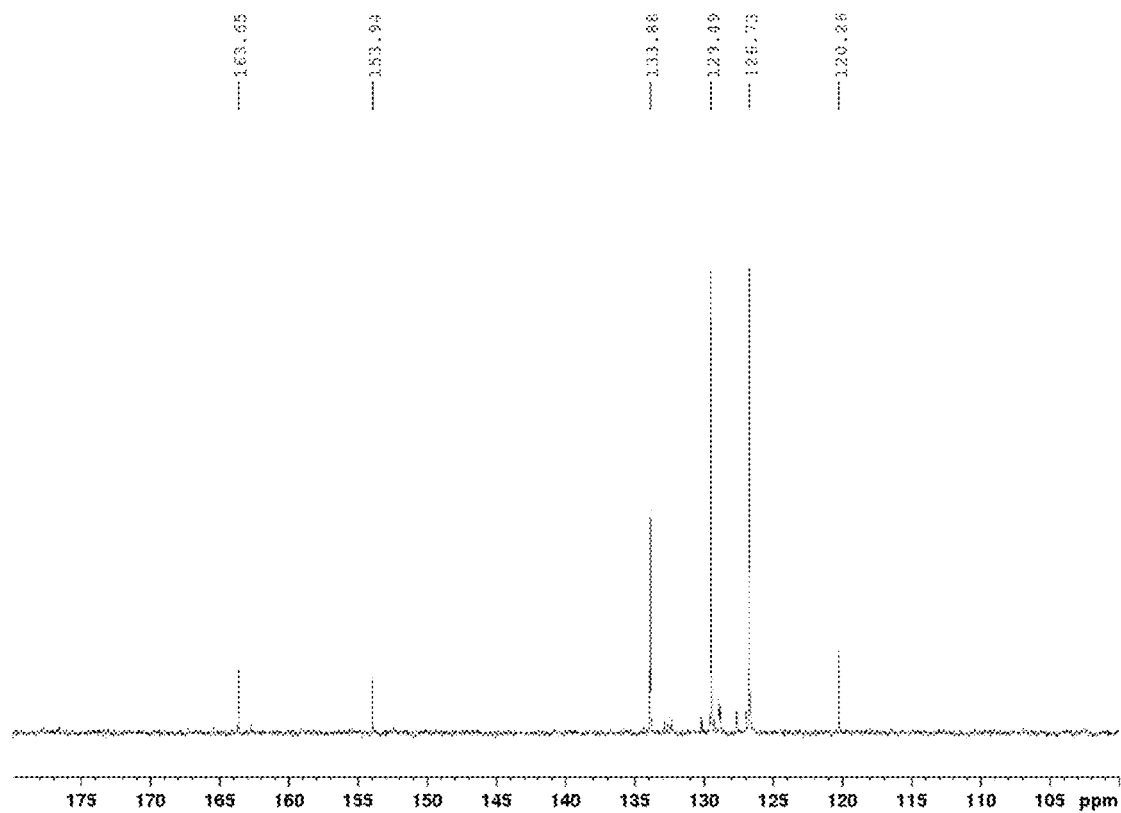
FIG. 2 is the $^{13}$C{$^1$H} NMR (CDCl$_3$, 125 MHz) spectrum for 3-phenyl-1,4,2-dioxazol-5-one prepared in accordance with an embodiment as described herein.

Compound 1 was confirmed to be 3-phenyl-1,4,2-dioxazol-5-one. The product was a white solid with a melting point of 63-65° C. and provided a yield of 20.3 g, 81%. The $^1$H NMR (CDCl$_3$, 300 MHz) is shown in FIG. 1 and indicates: δ=7.87 (dt, 2H, J=1.9 Hz, 8.9 Hz), 7.67 (tt, 1H, J=1.9 Hz, 8.9 Hz), 7.53 (tt, 2H, J=1.9 Hz, 8.9 Hz). The $^{13}$C{$^1$H} NMR (CDCl$_3$, 125 MHz) is shown in FIG. 2 and indicates: δ=163.7, 154.0, 133.9, 129.5, 126.8, 120.3.

Figure 3:
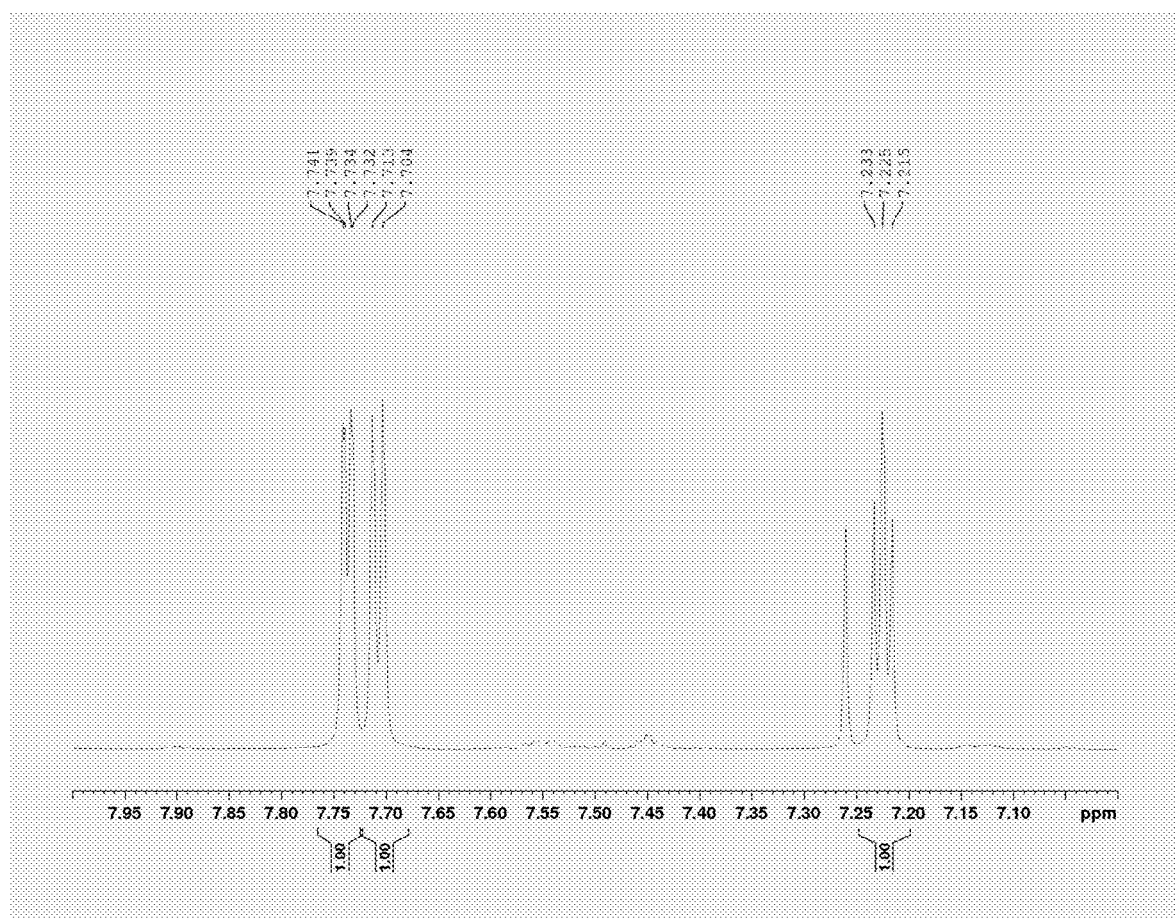
FIG. 3 is the $^1$H NMR (CDCl$_3$, 500 MHz) spectrum for 3-(2-thiophene)-1,4,2-dioxazol-5-one prepared in accordance with an embodiment as described herein.
Figure 4:
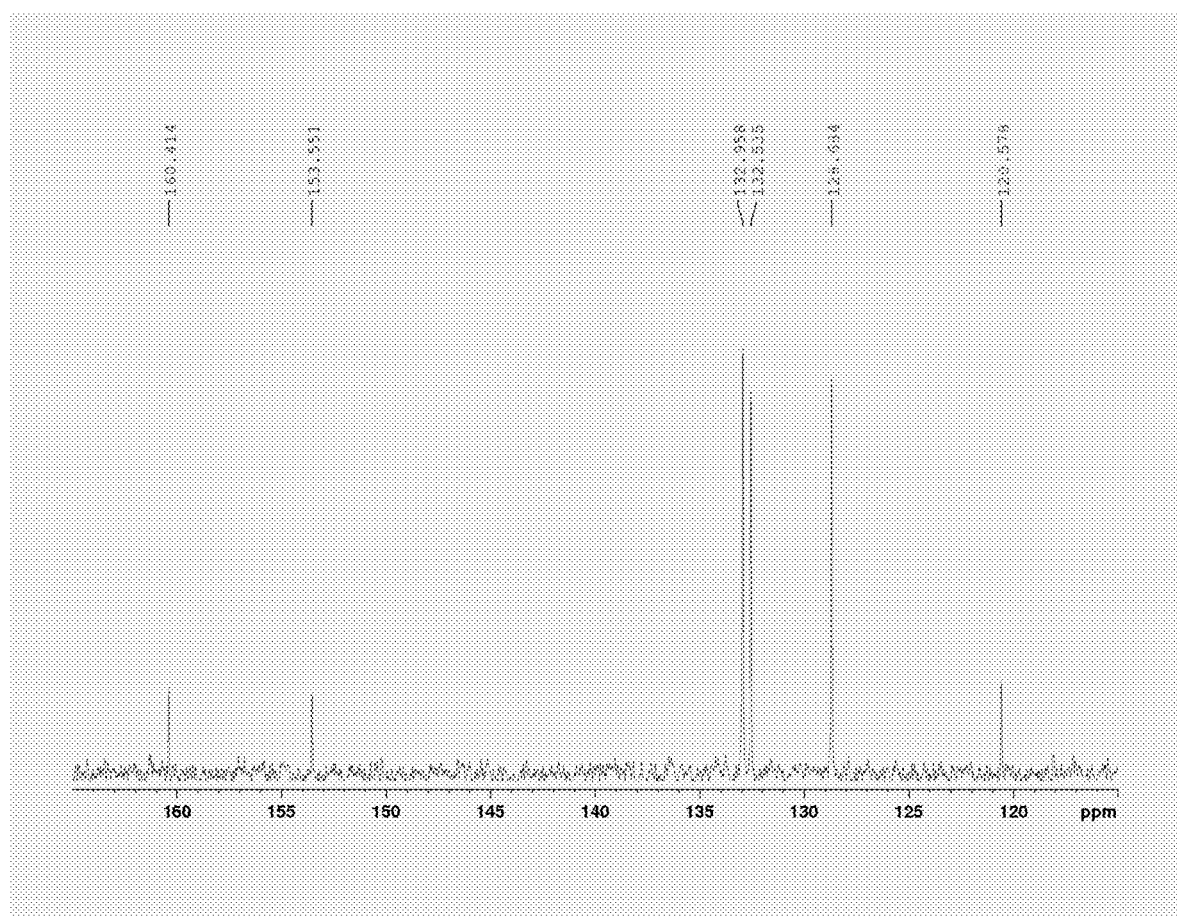
FIG. 4 is the $^{13}$C{$^1$H} NMR (CDCl$_3$, 75 MHz) spectrum for 3-(2-thiophene)-1,4,2-dioxazol-5-one prepared in accordance with an embodiment as described herein.

Compound 2 was confirmed to be 3-(2-thiophene)-1,4,2-dioxazol-5-one. The product was an off-white solid that decomposed rapidly above 192° C. and provided a yield of 1.53 g, 76%, The $^1$H NMR (CDCl$_3$, 500 MHz) spectrum is shown in FIG. 3 and indicates: δ=7.74 (dd, 1H, J=0.9 Hz, 3.8 Hz), 7.71 (dd, 1H, J=0.9 Hz, 4.9 Hz), 7.23 (dd, 1H, J=3.9 Hz, 4.8 Hz). The $^{13}$C{$^1$H} NMR (CDCl$_3$, 75 MHz) is shown in FIG. 4 and indicates: δ=160.4, 153.6, 133.0, 132.5, 128.7, 120.6.

Figure 5:
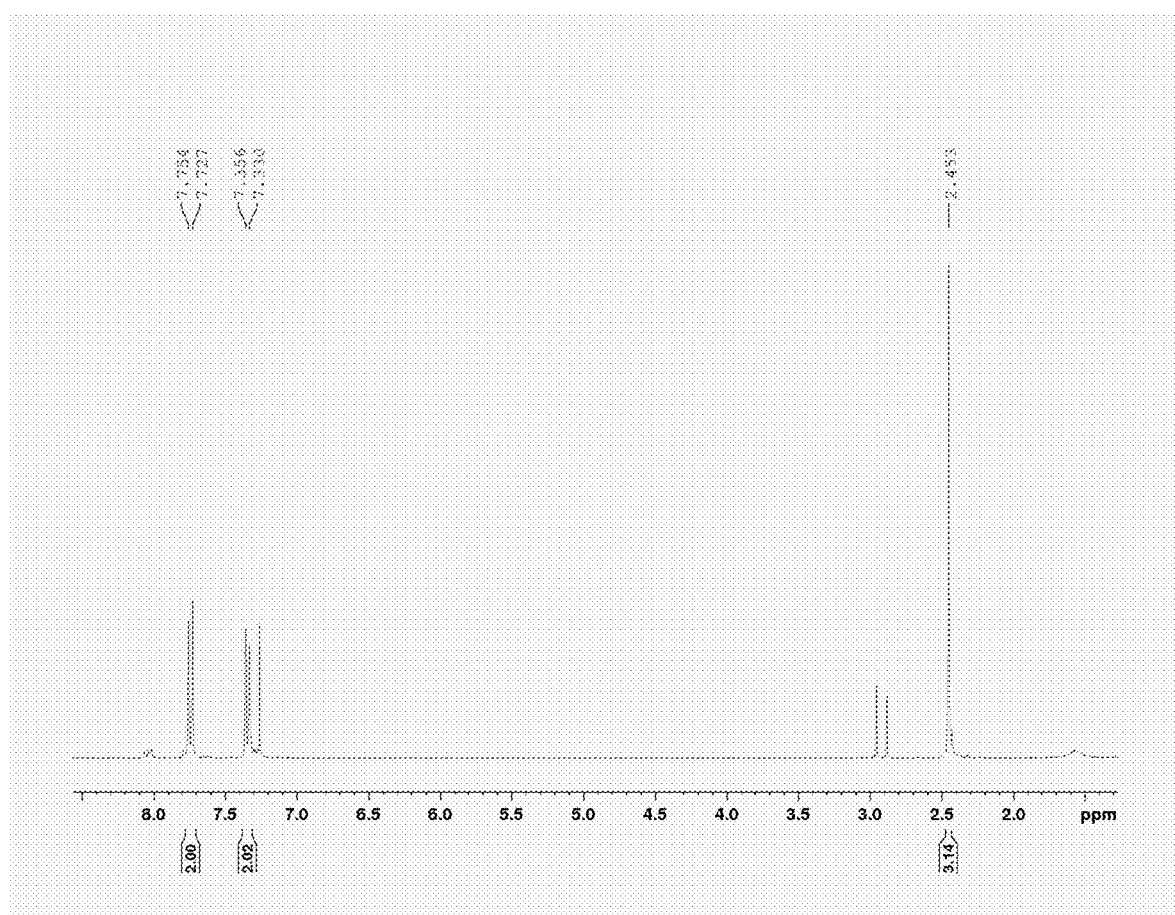
FIG. 5 is the $^1$H NMR (CDCl$_3$, 300 MHz) spectrum for 3-(p-tolyl)-1,4,2-dioxazol-5-one prepared in accordance with an embodiment as described herein.
Figure 6:
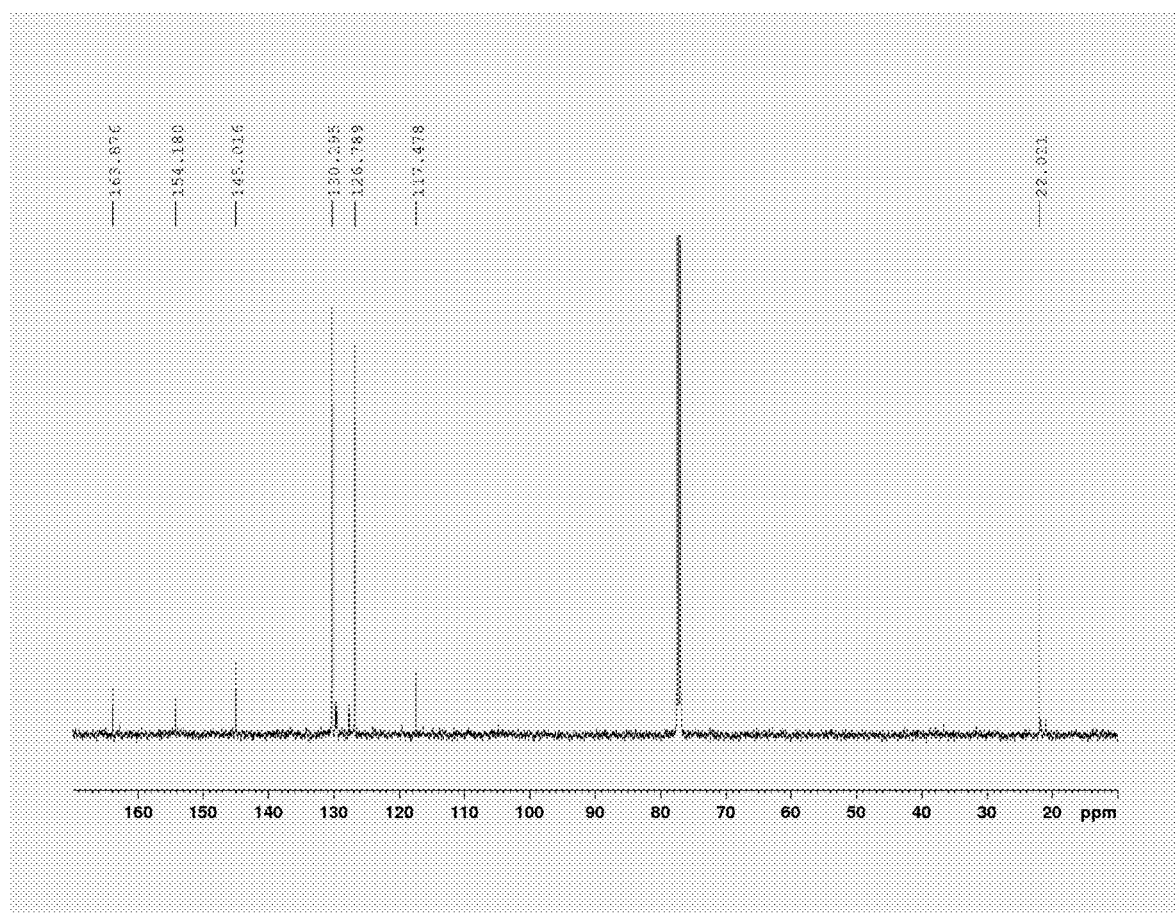
FIG. 6 is the $^{13}$C{$^1$H} NMR (CDCl$_3$, 125 MHz) spectrum for 3-(p-tolyl)-1,4,2-dioxazol-5-one prepared in accordance with an embodiment as described herein.

Compound 3 was confirmed to be 3-(p-tolyl)-1,4,2-dioxazol-5-one. The product was a a white solid with a melting point of 234-236° C. and provided a yield of 1.63 g, 77%. The $^1$H NMR (CDCl$_3$, 300 MHz) spectrum is shown in FIG. 5 and indicates: δ=7.74 (d, 2H, J=8.3 Hz), 7.35 (d, 2H, J=8.0 Hz), 2.45 (s, 3H). The $^{13}$C{$^1$H} NMR (CDCl$_3$, 125 MHz) spectrum is shown in FIG. 6 and indicates: 163.9, 154.2, 145.0, 130.3, 126.8, 117.5, 22.0.

Figure 7:
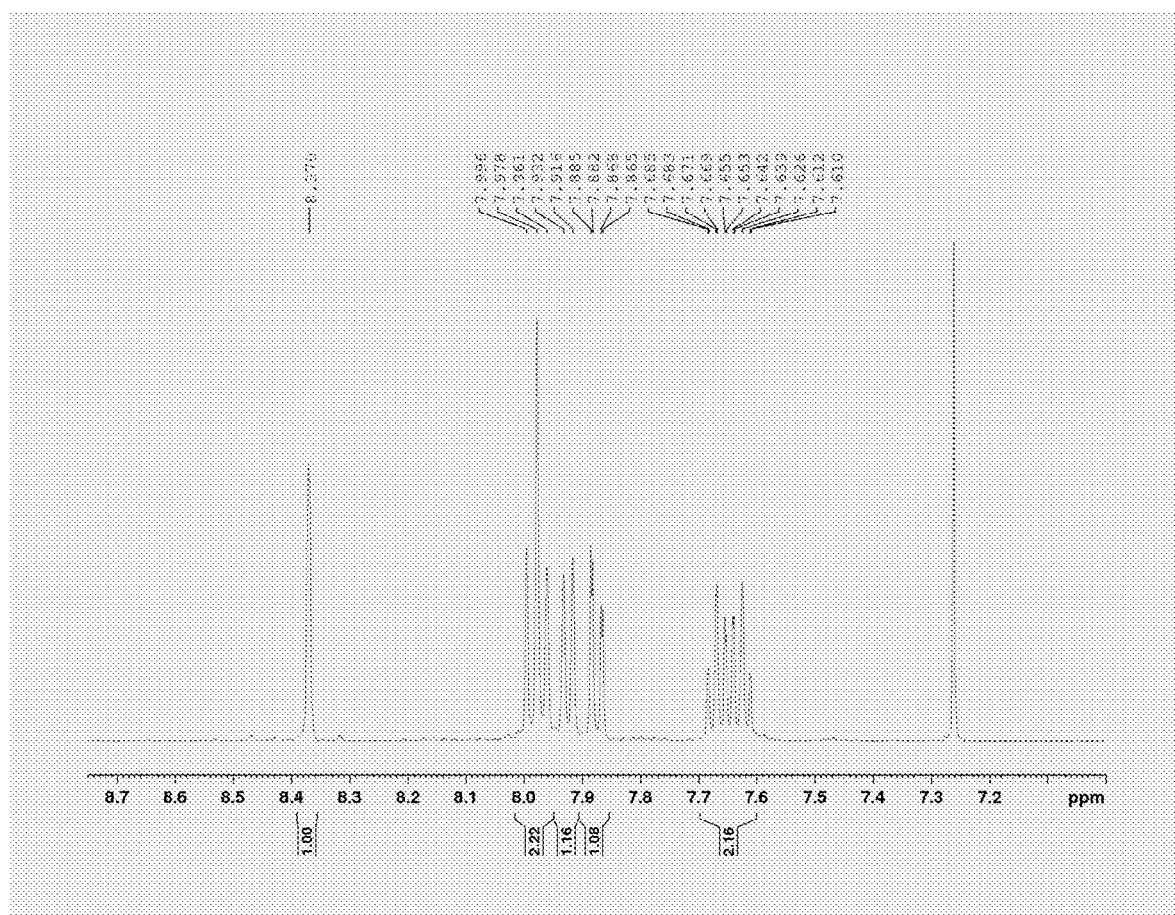
FIG. 7 is the $^1$H NMR (CDCl$_3$, 500 MHz) spectrum for 3-(2-naphthyl)-1,4,2-dioxazol-5-one prepared in accordance with an embodiment as described herein.
Figure 8:
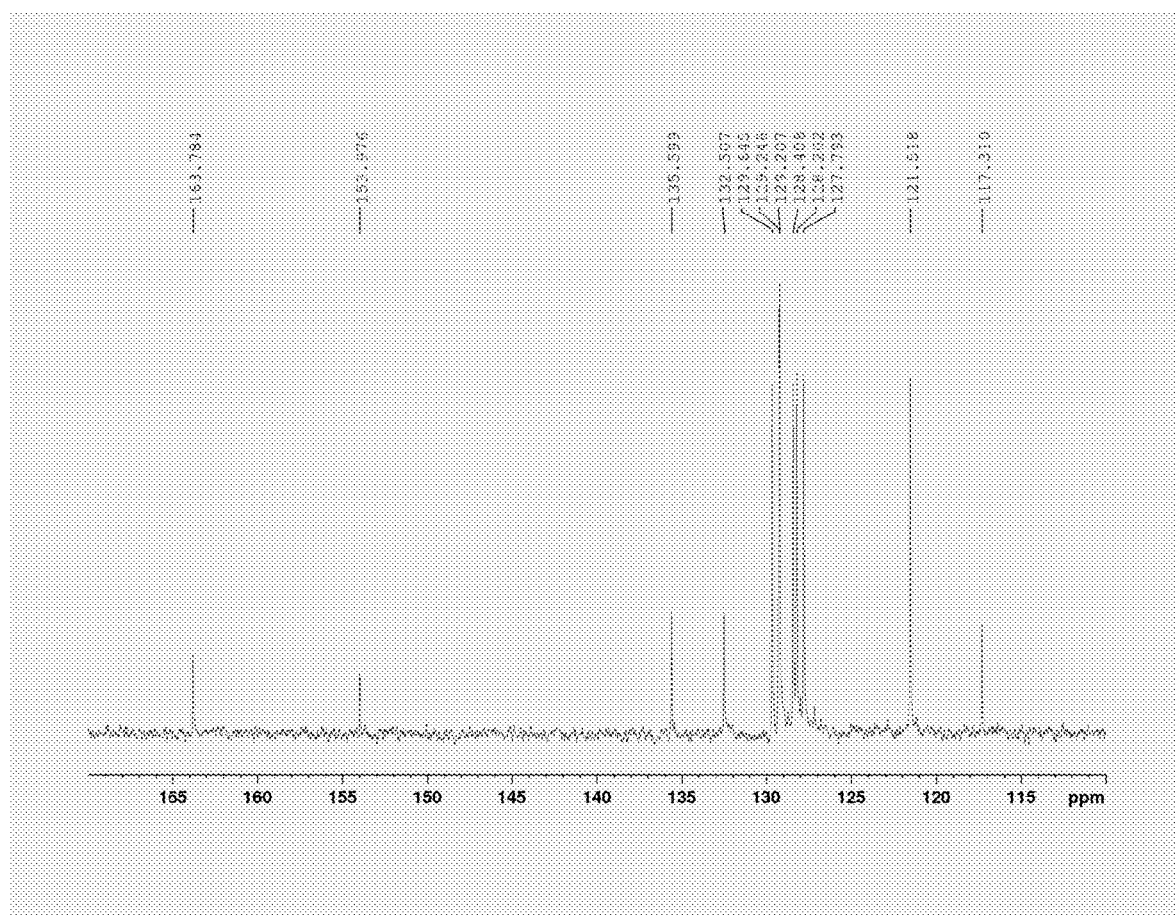
FIG. 8 is the $^{13}$C{$^1$H} NMR (CDCl$_3$, 125 MHz) spectrum for 3-(2-naphthyl)-1,4,2-dioxazol-5-one prepared in accordance with an embodiment as described herein.

Compound 4 was confirmed to be 3-(2-naphthyl)-1,4,2-dioxazol-5-one. The product was a white solid with a melting point of 108-109° C. and provided a yield of 2.15 g, 84%. The $^1$H NMR (CDCl$_3$, 500 MHz) spectrum is shown in FIG. 7 and indicates: δ=8.37 (br. s, 1H), 7.98 (t, 2H, J=8.8 Hz), 7.92 (d, 1H, J=8.1 Hz), 7.87 (dd, 1H, J=1.6 Hz, 8.5 Hz), 7.60-7.72 (m, 2H). The $^{13}$C{$^1$H} NMR (CDCl$_3$, 125 MHz) spectrum is shown FIG. 8 and indicates: δ=163.8, 154.0, 135.6, 132.5, 129.6, 129.3, 129.2, 128.4, 128.2, 127.8, 121.5, 117.3.

Figure 9:
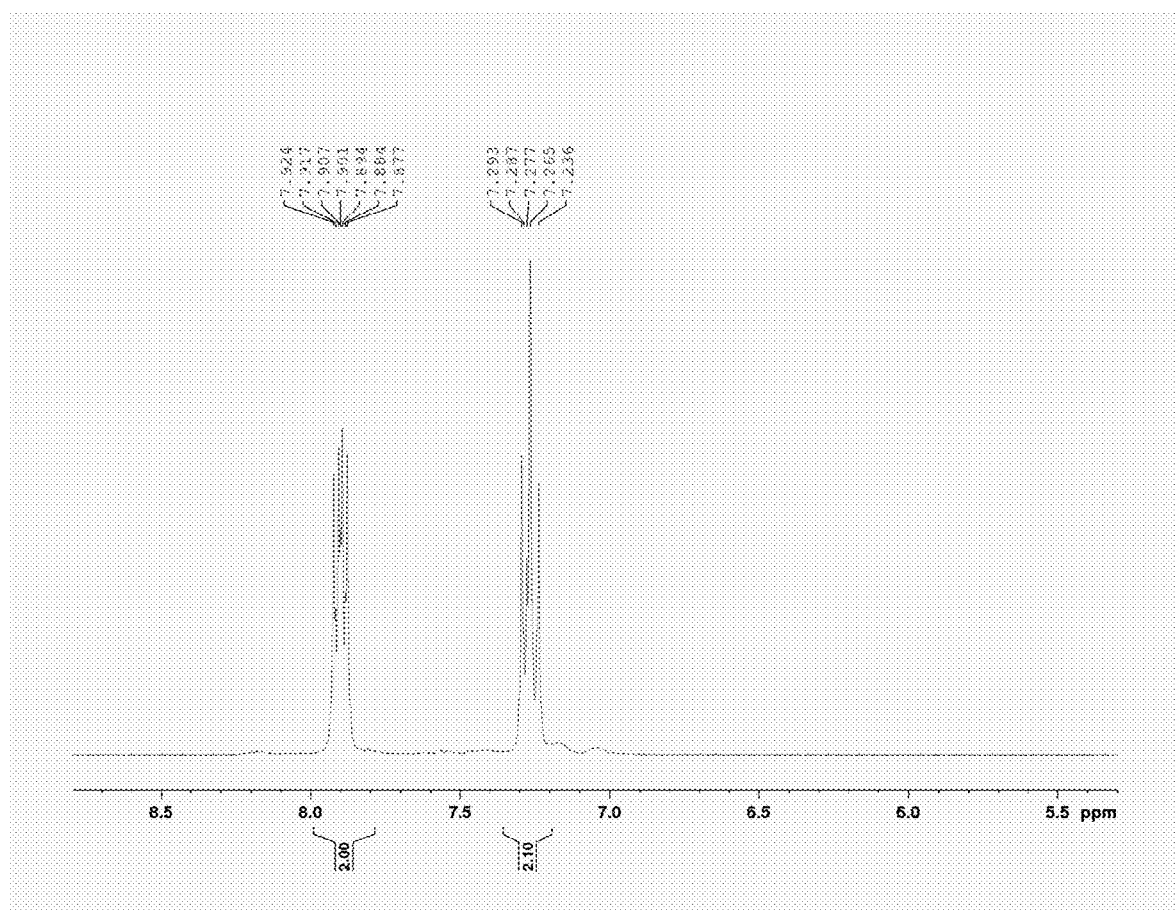
FIG. 9 is the $^1$H NMR (CDCl$_3$, 300 MHz) spectrum for 3-(p-fluorophenyl)-1,4,2-dioxazol-5-one prepared in accordance with an embodiment as described herein.
Figure 10:
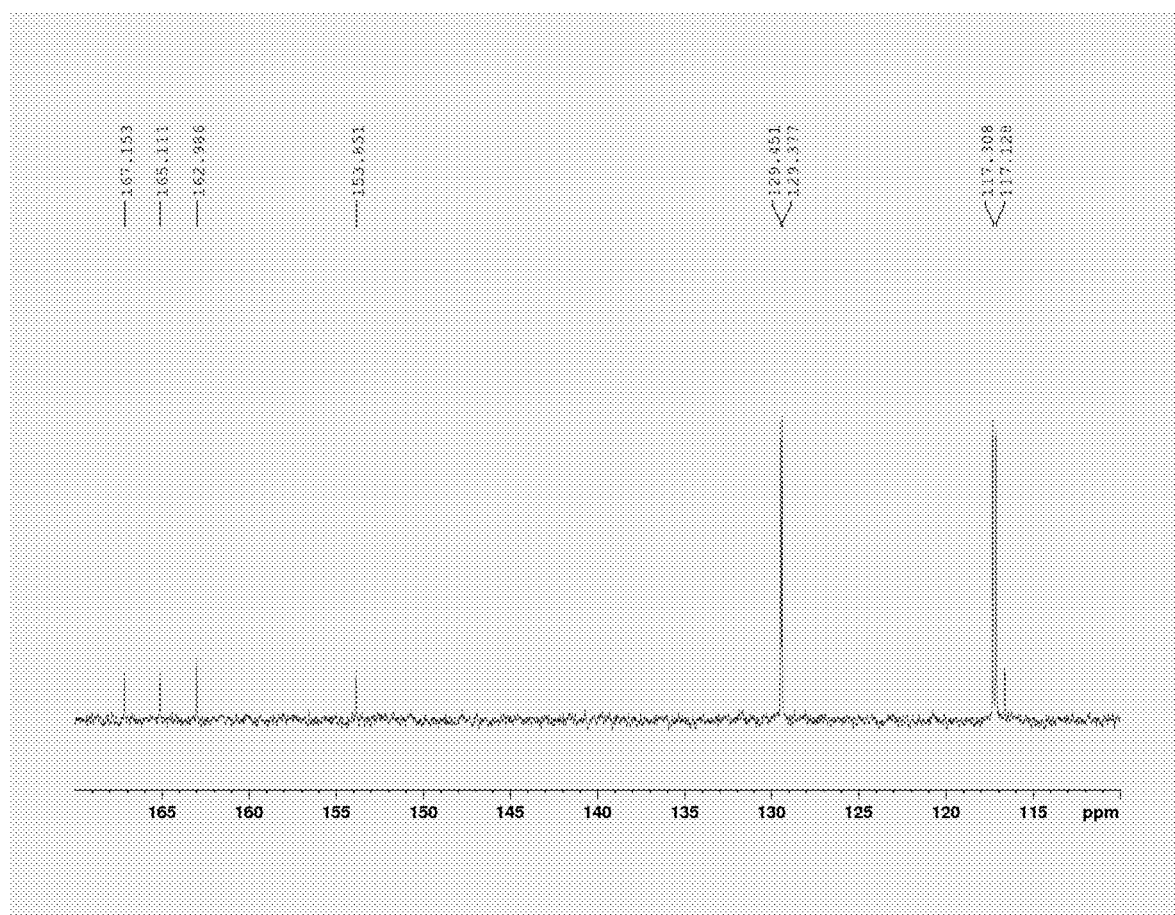
FIG. 10 is the $^{13}$C{$^1$H} NMR (CDCl$_3$, 125 MHz) spectrum for 3-(p-fluorophenyl)-1,4,2-dioxazol-5-one prepared in accordance with an embodiment as described herein.
Figure 11:
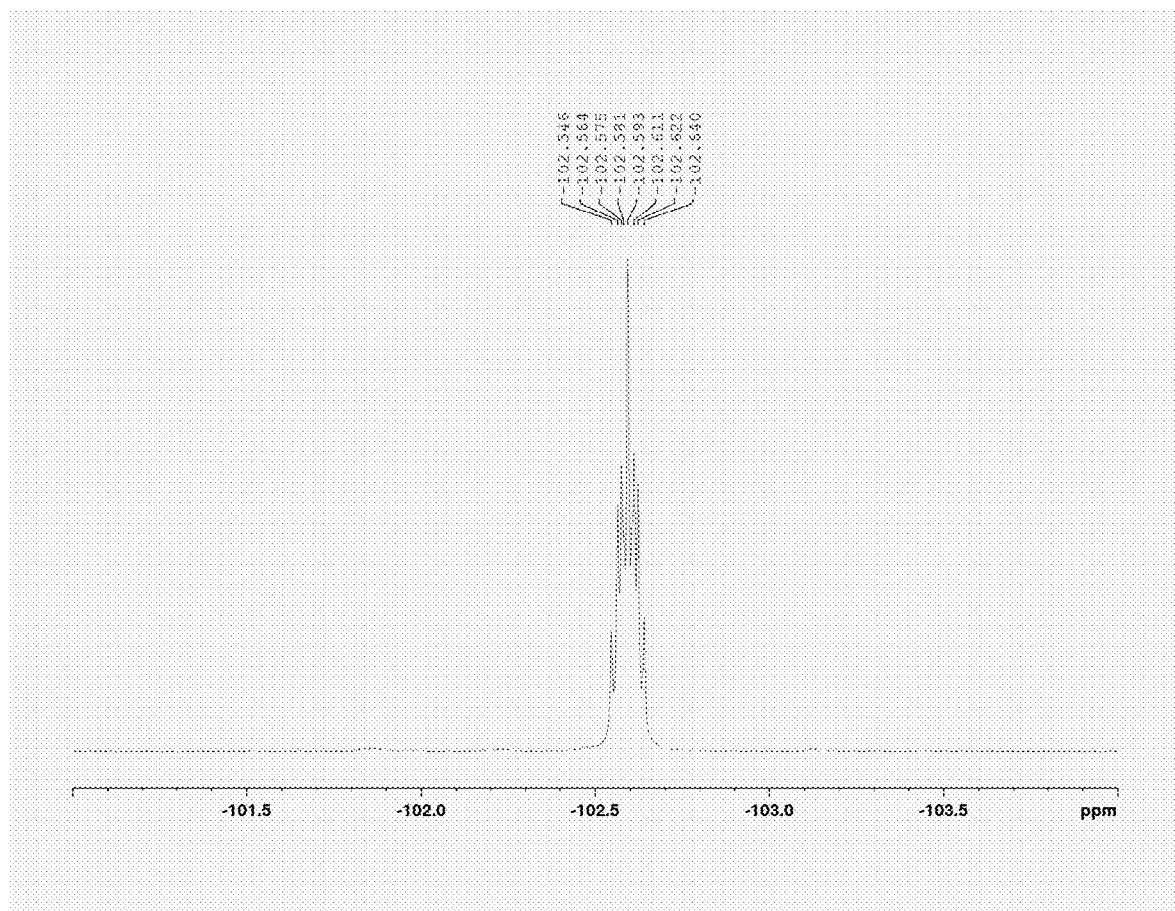
FIG. 11 is the $^{19}$F NMR (CDCl$_3$, 282 MHz) spectrum for 3-(p-fluorophenyl)-1,4,2-dioxazol-5-one prepared in accordance with an embodiment as described herein.

Compound 5 was confirmed to be 3-(p-fluorophenyl)-1,4,2-dioxazol-5-one. The product was a white solid with a melting point of 66-68° C. and provided a yield of 1.07 g, 49%. The $^1$H NMR (CDCl$_3$, 300 MHz) spectrum is shown in FIG. 9 and indicates: δ=7.93-7.84 (m, 2H), 7.30-7.20 (m, 2H). The $^{13}$C{$^1$H} NMR (CDCl$_3$, 125 MHz) spectrum is shown in FIG. 10 and indicates: δ=167.1, 165.1, 163.0, 153.9, 129.4 (d, J=9.3 Hz), 117.2 (d, J=23.1 Hz). The $^{19}$F NMR (CDCl$_3$, 282 MHz) spectrum is shown in FIG. 11 and indicates: δ=-102.6 (m).

Figure 12:
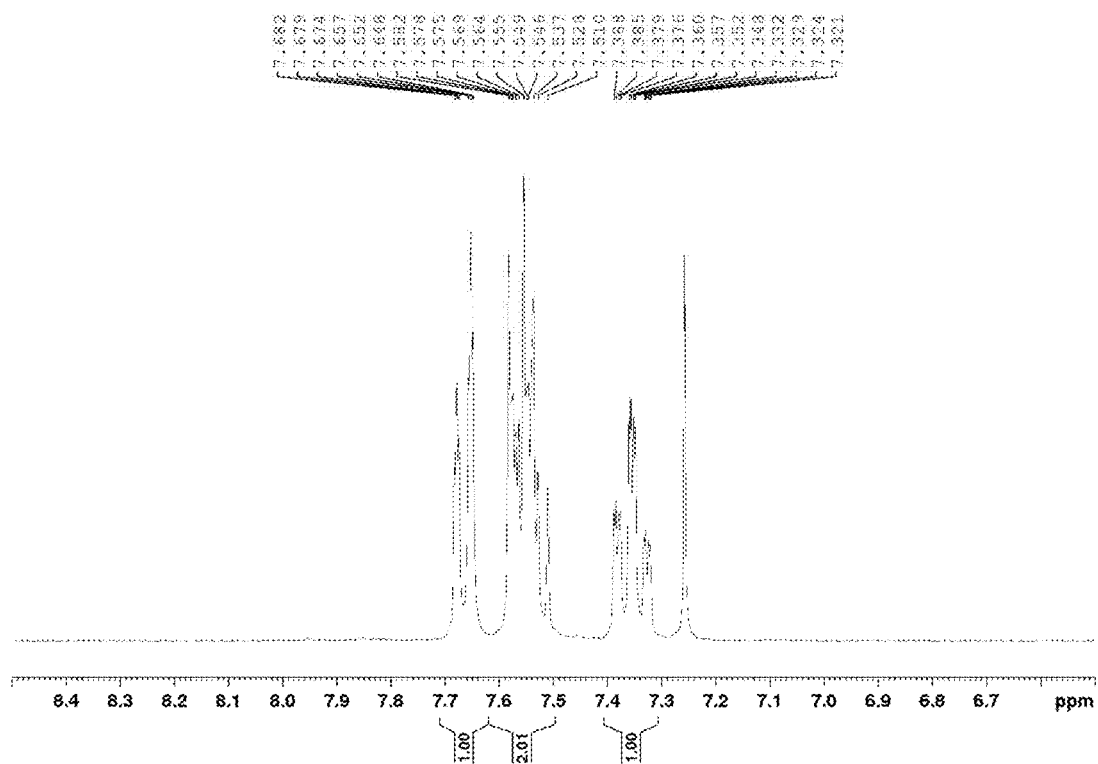
FIG. 12 is the $^1$H NMR (CDCl$_3$, 300 MHz) spectrum for 3-(m-fluorophenyl)-1,4,2-dioxazol-5-one prepared in accordance with an embodiment as described herein.
Figure 13:
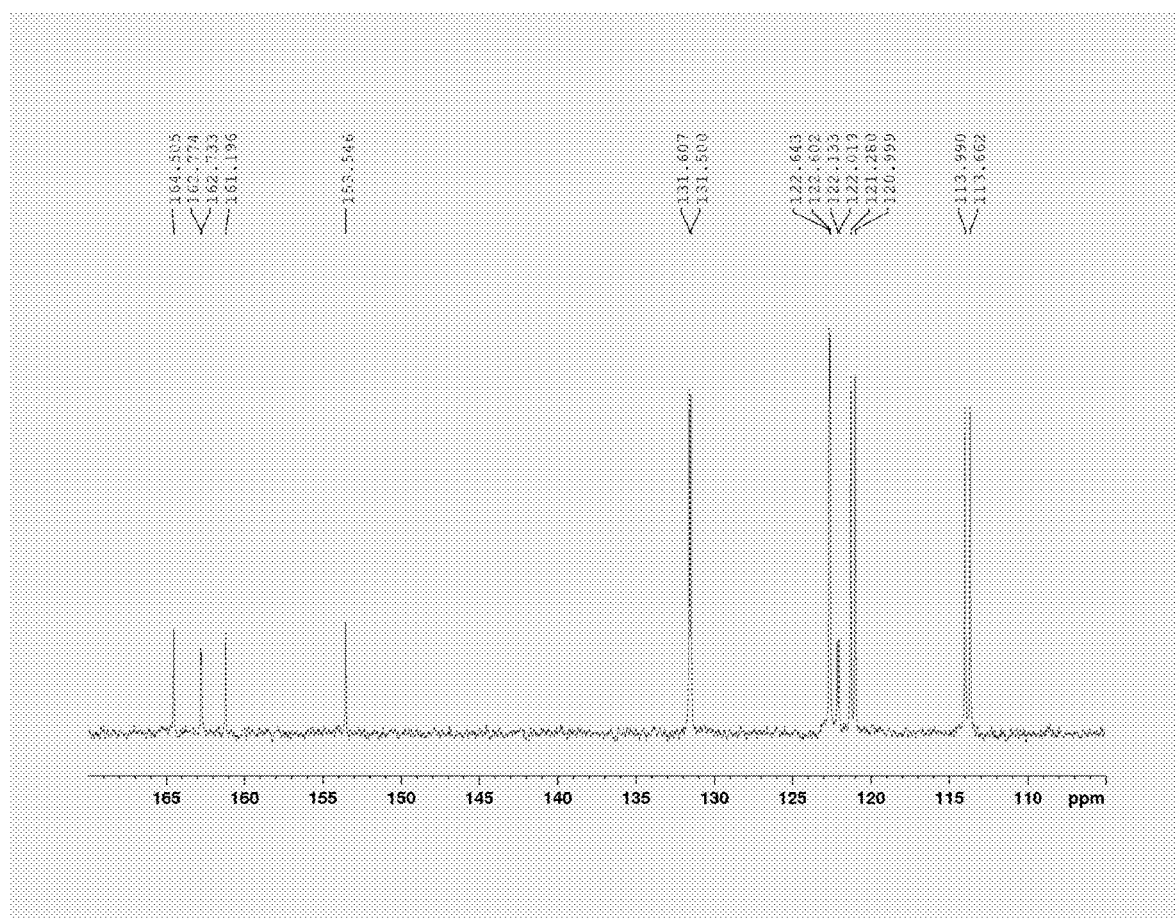
FIG. 13 is the $^{13}$C{$^1$H} NMR (CDCl$_3$, 75 MHz) spectrum for 3-(m-fluorophenyl)-1,4,2-dioxazol-5-one prepared in accordance with an embodiment as described herein.
Figure 14:
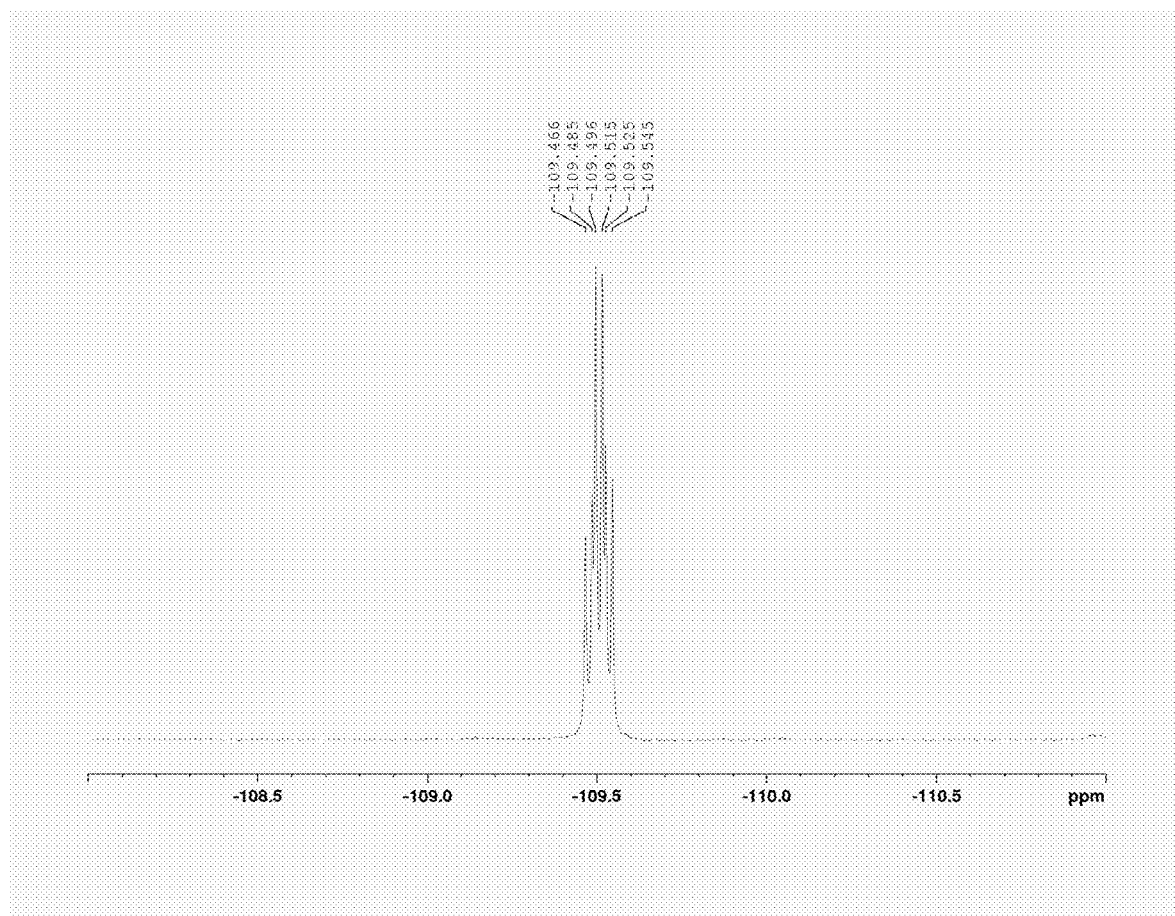
FIG. 14 is the $^{19}$F NMR (CDCl$_3$, 282 MHz) spectrum for 3-(m-fluorophenyl)-1,4,2-dioxazol-5-one prepared in accordance with an embodiment as described herein.

Compound 6 was confirmed to be 3-(m-fluorophenyl)-1,4,2-dioxazol-5-one. The product was a white solid with a melting point of 64-65° C. and provided a yield of 1.11 g, 51%. The $^1$H NMR (CDCl$_3$, 300 MHz) spectrum is shown in FIG. 12 and indicates: δ=7.67 (dt, 1H, J=1.3 Hz, 7.8 Hz), 7.63-7.69 (m, 2H), 7.35 (t, 1H, J=7.6 Hz). The $^{13}$C{$^1$H} NMR (CDCl$_3$, 75 MHz) spectrum is shown in FIG. 13 and indicates: δ=162.9 (d, J=248 Hz), 162.8 (d, J=3.1 Hz), 153.5, 131.5 (d, J=8.1 Hz), 122.6 (d, J=3.0 Hz), 122.4 (d, J=8.6 Hz), 121.1 (d, J=21.3 Hz), 113.8 (d, J=24.8 Hz). The $^{19}$F NMR (CDCl$_3$, 282 MHz) spectrum is shown in FIG. 14 and indicates: δ=-106.9 (m).

Figure 15:
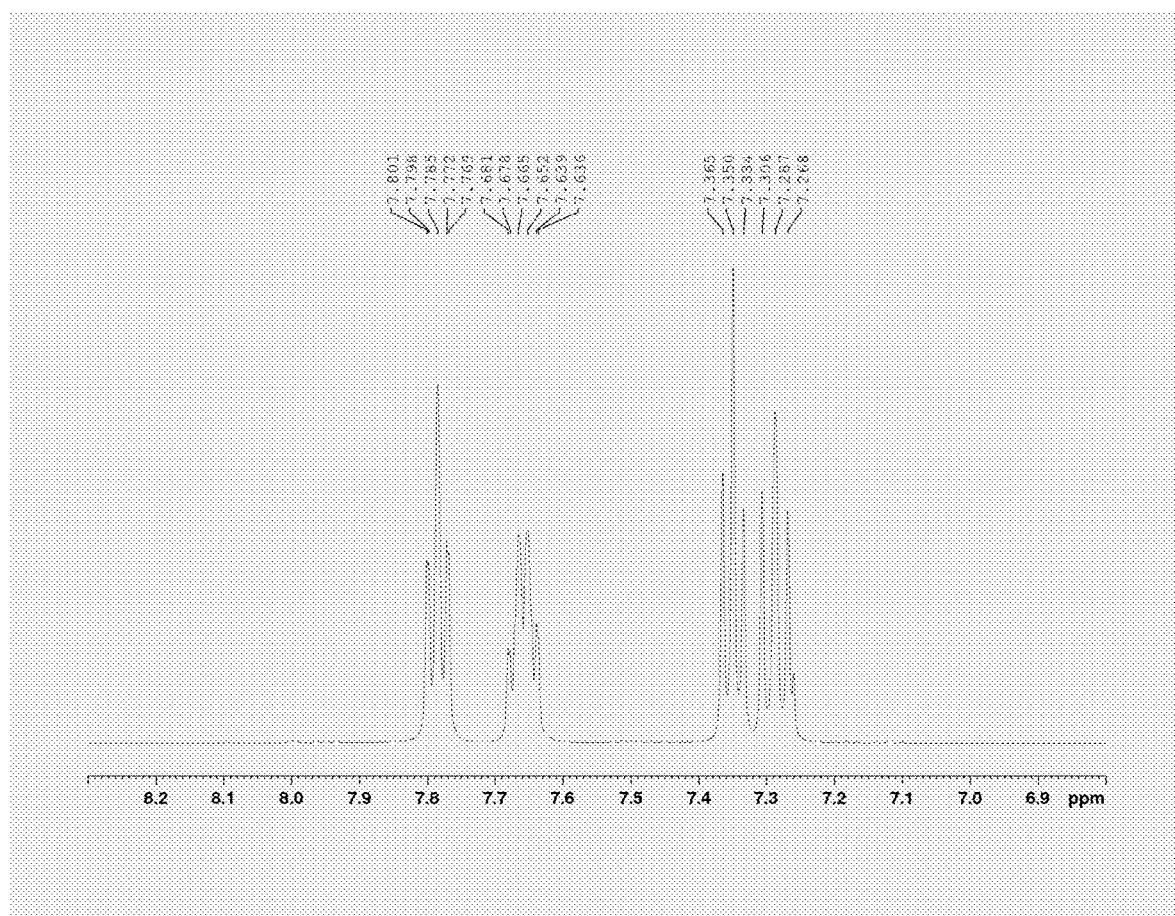
FIG. 15 is the $^1$H NMR (CDCl$_3$, 500 MHz) spectrum for 3-(o-fluorophenyl)-1,4,2-dioxazol-5-one prepared in accordance with an embodiment as described herein.
Figure 16:
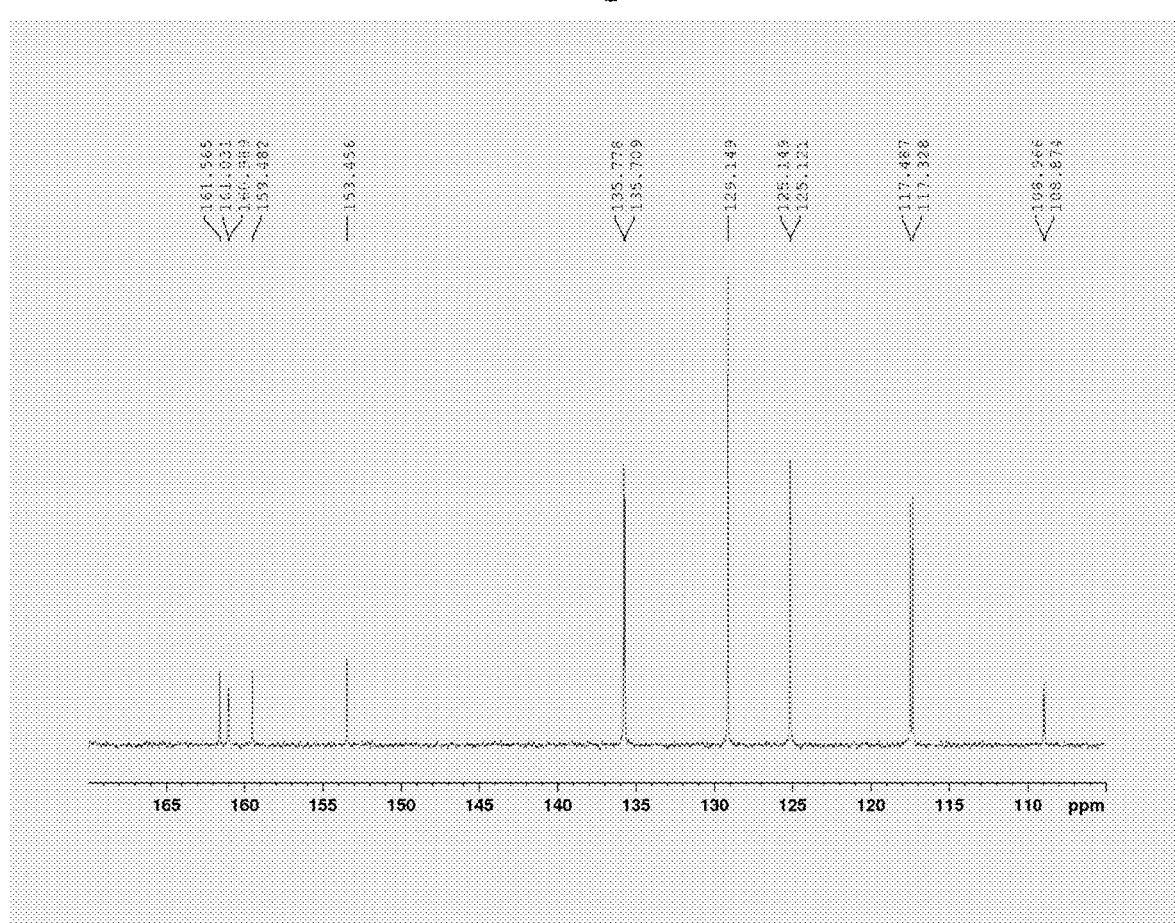
FIG. 16 is the $^{13}$C{$^1$H} NMR (CDCl$_3$, 125 MHz) spectrum for 3-(o-fluorophenyl)-1,4,2-dioxazol-5-one prepared in accordance with an embodiment as described herein.
Figure 17:
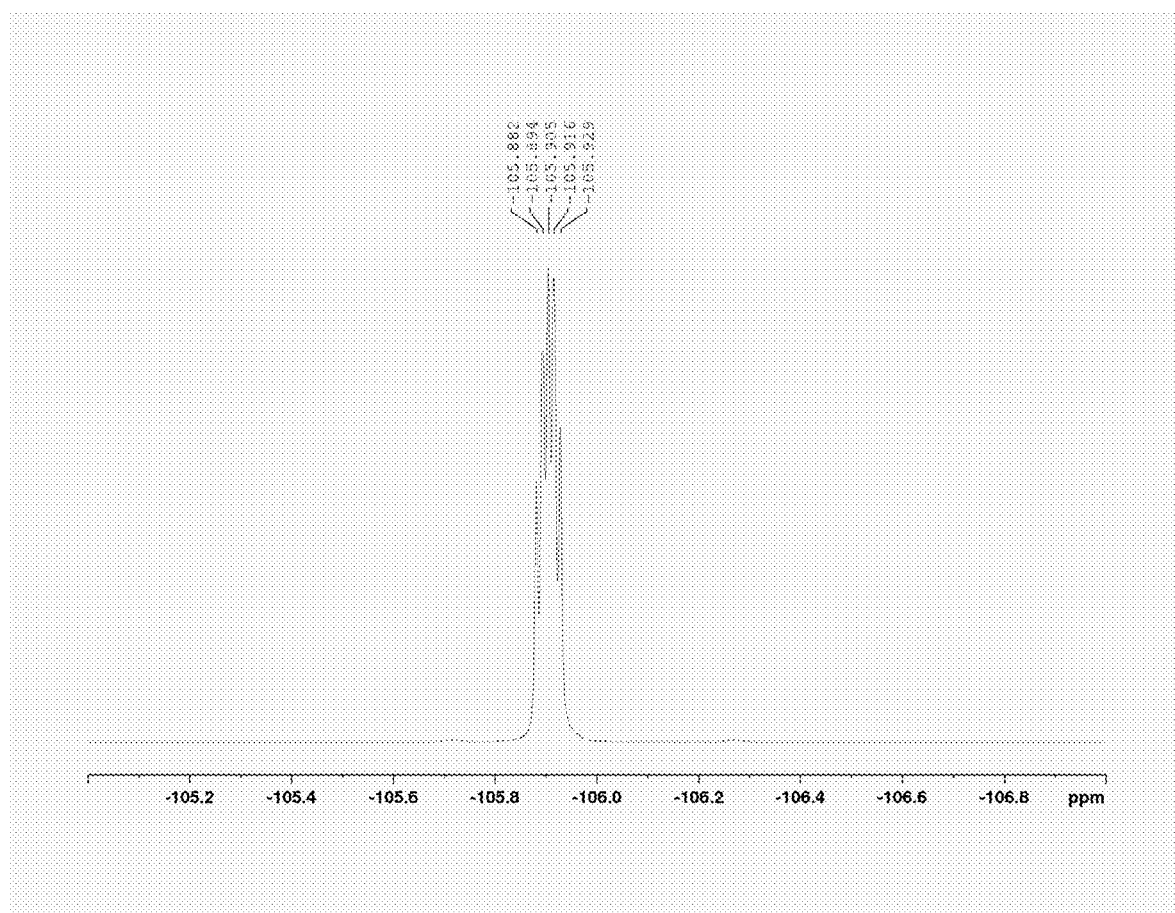
FIG. 17 is the $^{19}$F NMR (CDCl$_3$, 470 MHz) spectrum for 3-(o-fluorophenyl)-1,4,2-dioxazol-5-one prepared in accordance with an embodiment as described herein.

Compound 7 was confirmed to be 3-(o-fluorophenyl)-1,4,2-dioxazol-5-one. The product was a white solid with a melting point of 79-80° C. and provided a yield of 1.53 g, 70%. The $^1$H NMR (CDCl$_3$, 500 MHz) spectrum is shown in FIG. 15 and indicates: δ=7.79 (td, 1H, J=1.3 Hz, 7.9 Hz), 7.50-7.59 (m, 2H), 7.35 (tdd, 1H, J=0.9 Hz, 2.6 Hz, 8.3 Hz). The $^{13}$C {$^1$H} NMR (CDCl$_3$, 125 MHz) spectrum is shown in FIG. 16 and indicates: δ=161.0 (d, J=5.4 Hz), 160.5 (d, J=156 Hz), 153.5, 135.7 (d, J=8.7 Hz), 129.1, 125.1 (d, J=3.5 Hz), 117.4 (d, J=19.8 Hz), 108.9 (d, J=11.5 Hz). The $^{19}$F NMR (CDCl$_3$, 470 MHz) spectrum is shown in FIG. 17 and indicates: δ=-105.9 (m).

Figure 18:
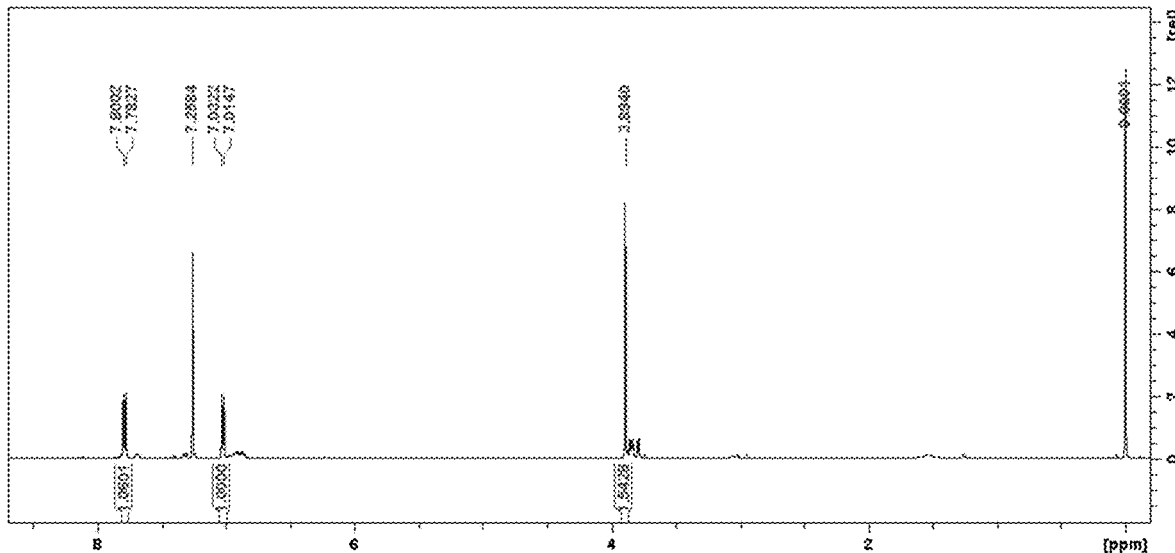
FIG. 18 is the $^1$H NMR (CDCl$_3$, 500 MHz) spectrum for 3-(p-methoxyphenyl)-1,4,2-dioxazol-5-one prepared in accordance with an embodiment as described herein.
Figure 19:
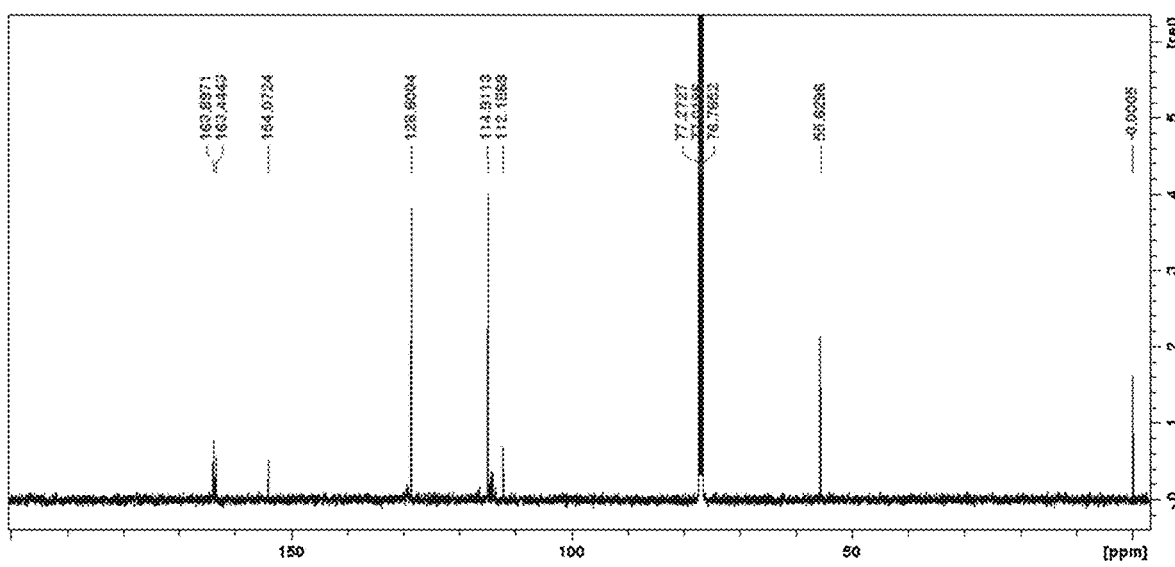
FIG. 19 is the $^{13}$C{$^1$H} NMR (CDCl$_3$, 125 MHz) spectrum for 3-(p-methoxyphenyl)-1,4,2-dioxazol-5-one prepared in accordance with an embodiment as described herein.

Compound 8 was confirmed to be 3-(p-methoxy)-1,4,2-dioxazol-5-one. The product was a white solid with a melting point of 152-153° C. and provided a yield of 1.53 g, 63%. The $^1$H NMR (CDCl$_3$, 500 MHz) spectrum is shown in FIG. 18 and indicates: δ=7.79 (d, 2H, J=8.7 Hz), 7.02 (d, 2H, J=8.7 Hz), 3.89 (s, 3H). The $^{13}$C{$^1$H} NMR (CDCl$_3$, 125 MHz) spectrum is shown in FIG. 19 and indicates: 163.9, 163.4 154.1, 128.6, 114.9, 112.2, 55.6.

Figure 20:
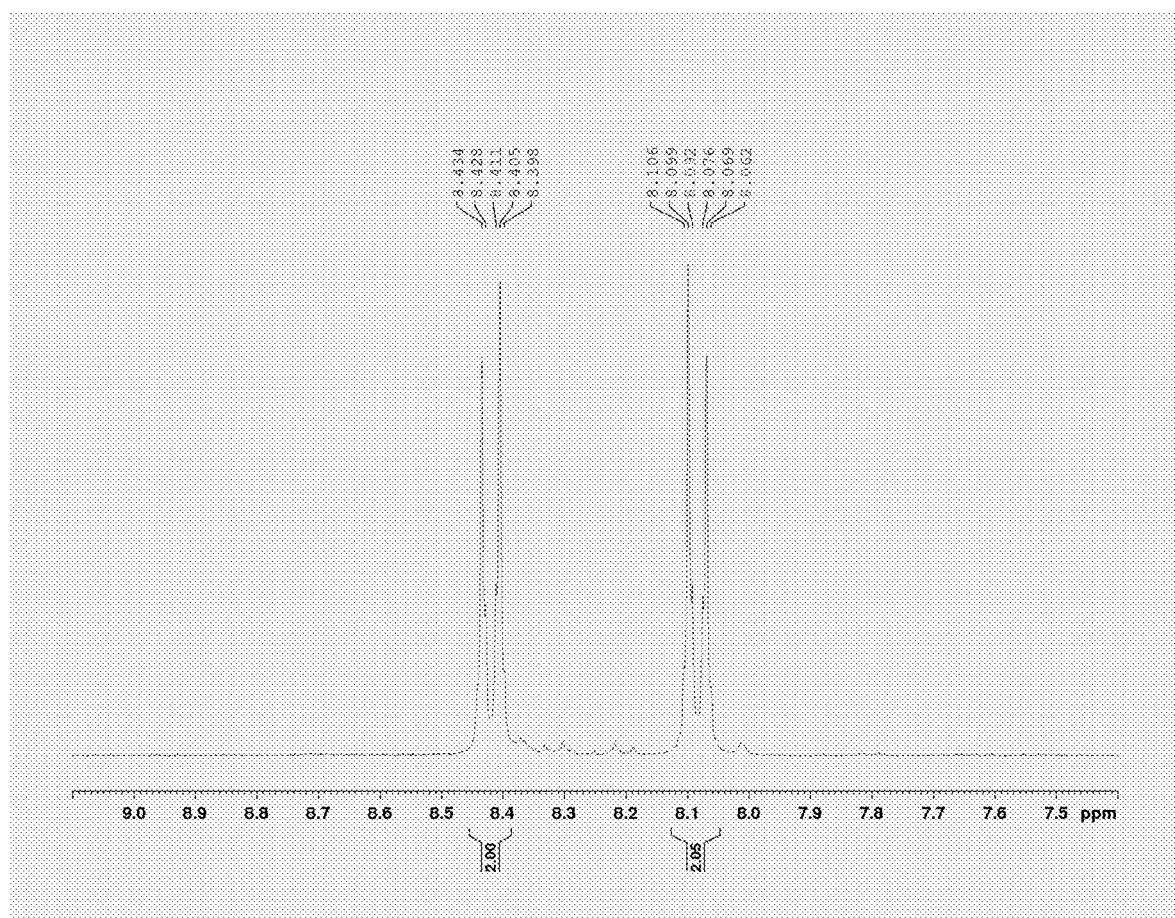
FIG. 20 is the $^1$H NMR (CDCl$_3$, 300 MHz) spectrum for 3-(p-nitrophenyl)-1,4,2-dioxazol-5-one prepared in accordance with an embodiment as described herein.
Figure 21:
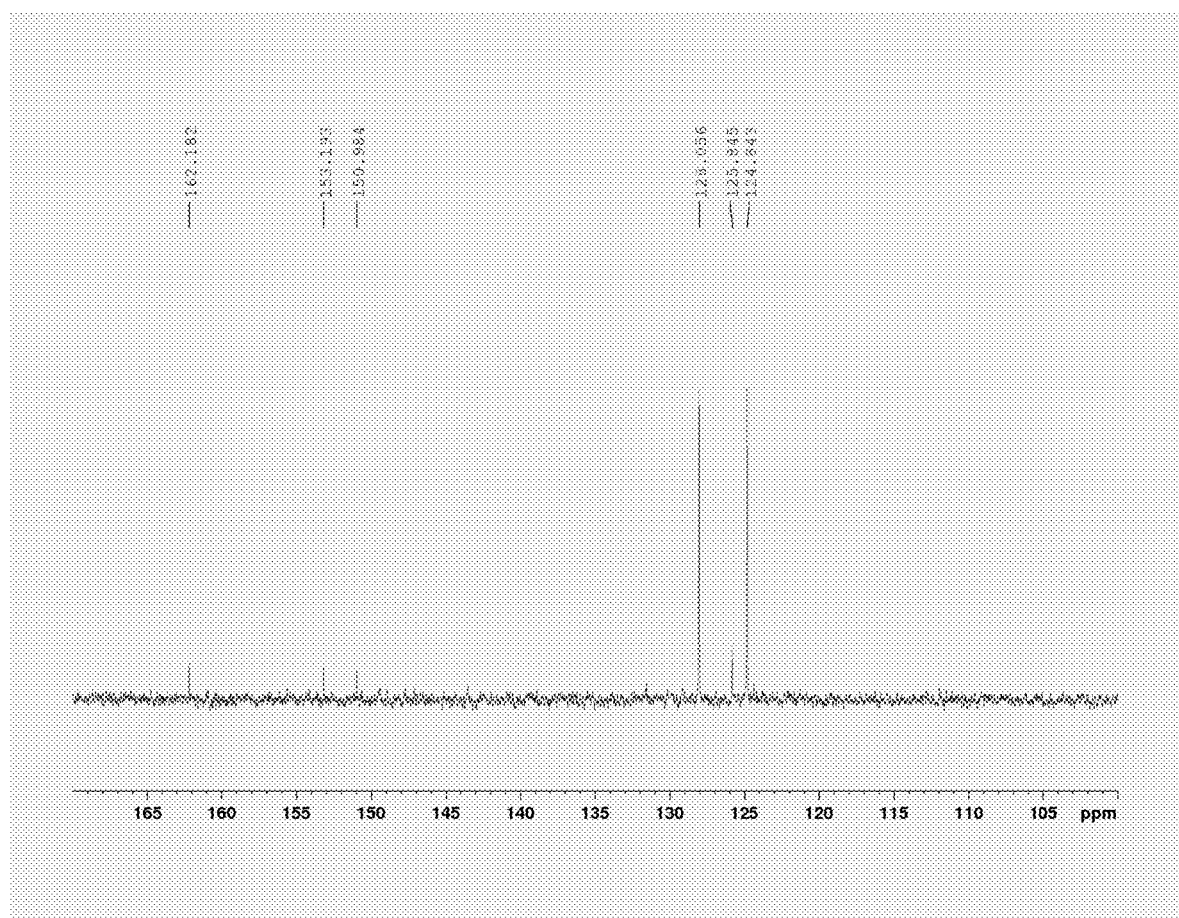
FIG. 21 is the $^{13}$C{$^1$H} NMR (CDCl$_3$, 125 MHz) spectrum for 3-(p-nitrophenyl)-1,4,2-dioxazol-5-one prepared in accordance with an embodiment as described herein.

Compound 9 was confirmed to be 3-(p-nitrophenyl)-1,4,2-dioxazol-5-one. The product was a yellow solid with a melting point of 160-162° C. and provided a yield of 1.95 g, 78%. The $^1$H NMR (CDCl$_3$, 300 MHz) spectrum is shown in FIG. 20 and indicates: δ=8.42 (dt, 2H, J=1.9 Hz, 8.9 Hz), 8.08 (dt, 2H, J=1.9 Hz, 8.9 Hz). The $^{13}$C {$^1$H} NMR (CDCl$_3$, 125 MHz) spectrum is shown in FIG. 21 and indicates: δ=162.2, 153.2, 151.0, 128.1, 125.8, 124.8

Figure 22:
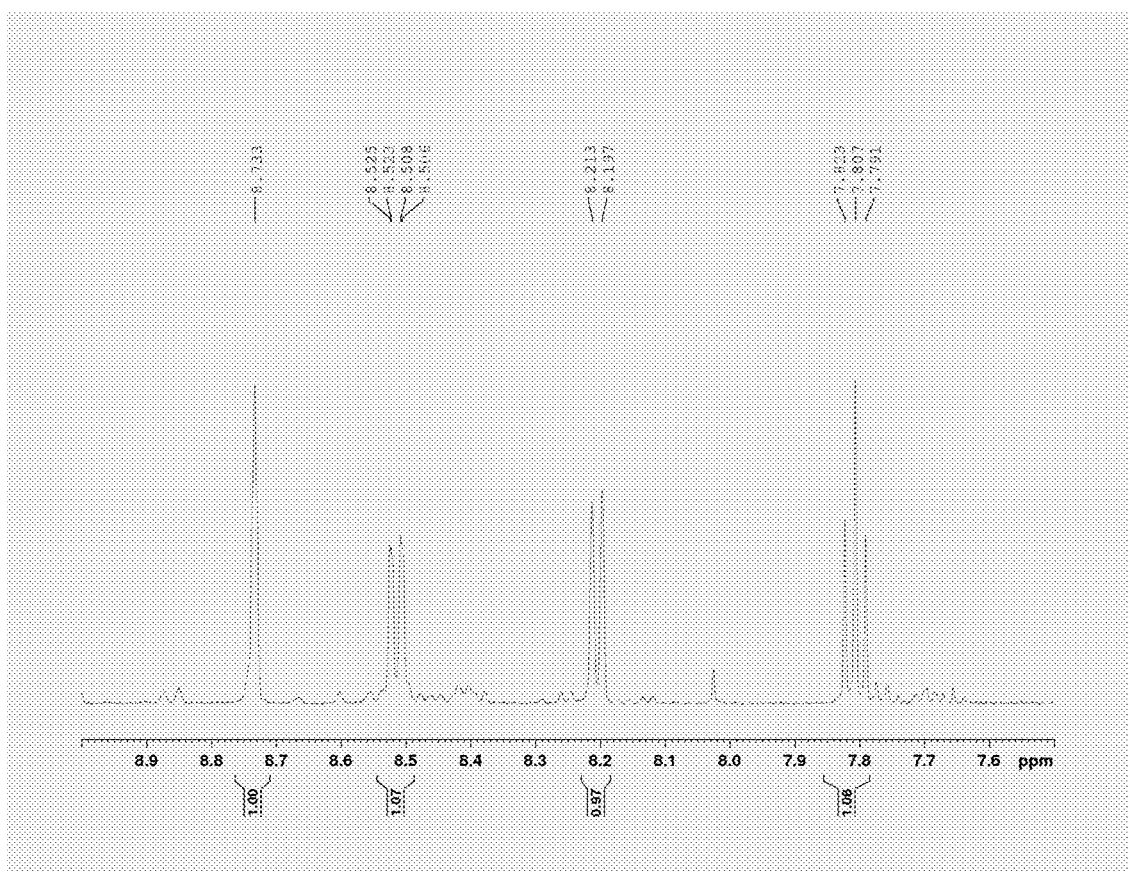
FIG. 22 is the $^1$H NMR (CDCl$_3$, 300 MHz) spectrum for 3-(m-nitrophenyl)-1,4,2-dioxazol-5-one prepared in accordance with an embodiment as described herein.
Figure 23:
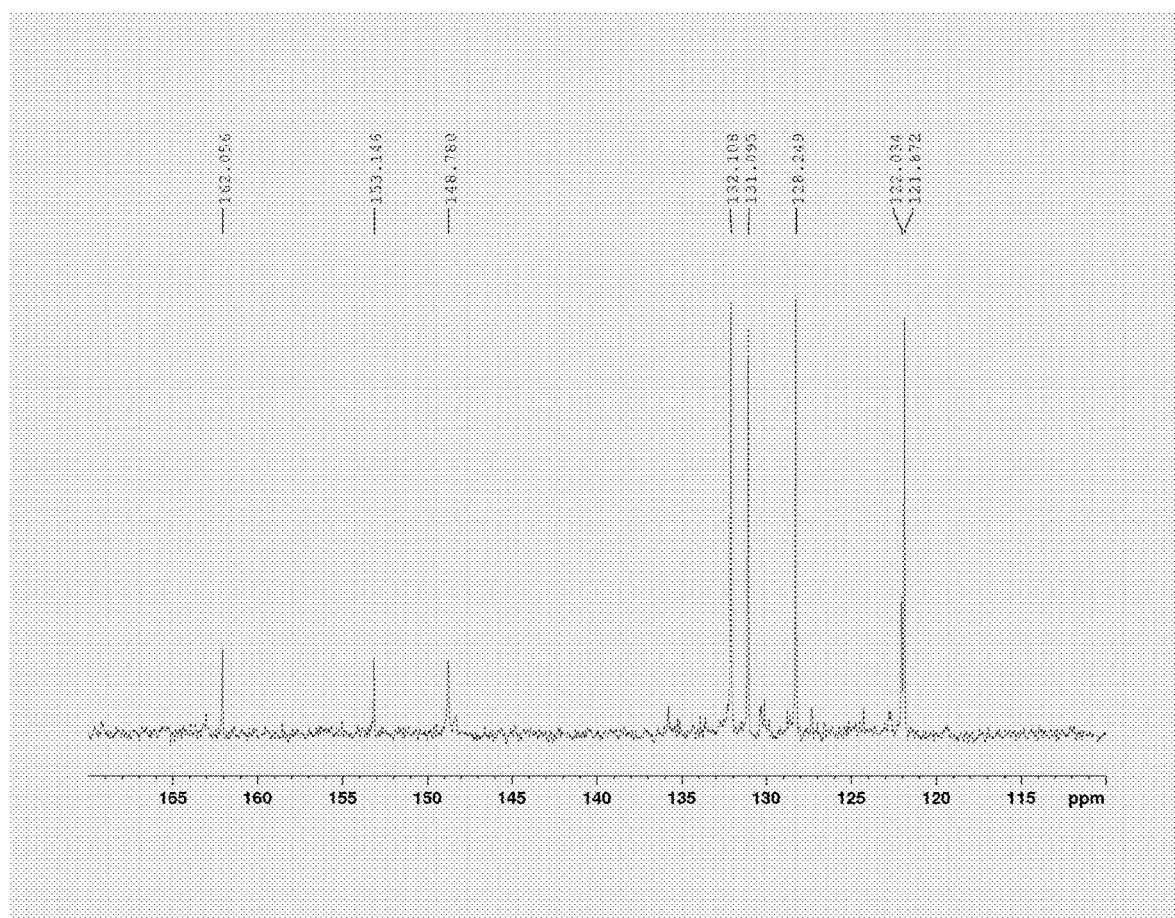
FIG. 23 is the $^{13}$C{$^1$H} NMR (CDCl$_3$, 75 MHz) spectrum for 3-(m-nitrophenyl)-1,4,2-dioxazol-5-one prepared in accordance with an embodiment as described herein.

Compound 10 was confirmed to be 3-(m-nitrophenyl)-1,4,2-dioxazol-5-one. The product was a yellow solid with a melting point of 94-96° C. and provided a yield of 1.44 g, 58%. The $^1$H NMR (CDCl$_3$, 300 MHz) spectrum is shown in FIG. 22 and indicates: δ=8.73 (t, J=1.7 Hz), 8.46-8.53 (m, 1H), 8.18-8.23 (m, 1H), 7.79 (t, 1H, J=7.9 Hz). The $^{13}$C{$^1$H} NMR (CDCl$_3$, 75 MHz) spectrum is shown in FIG. 23 and indicates: δ=162.1, 153.1, 148.8, 132.1, 131.1, 128.2, 122.0, 121.9.

Figure 24:
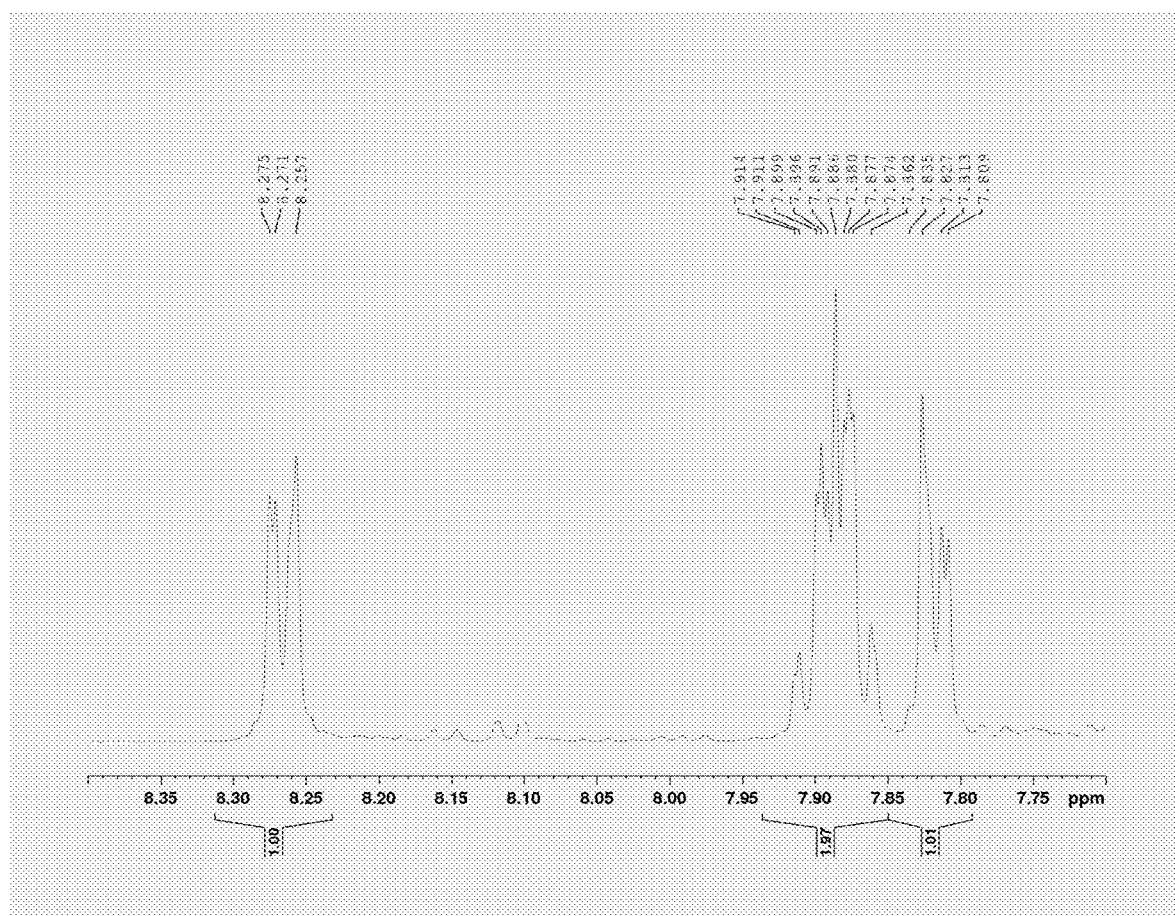
FIG. 24 is the $^1$H NMR (CDCl$_3$, 500 MHz) spectrum for 3-(o-nitrophenyl)-1,4,2-dioxazol-5-one prepared in accordance with an embodiment as described herein.
Figure 25:
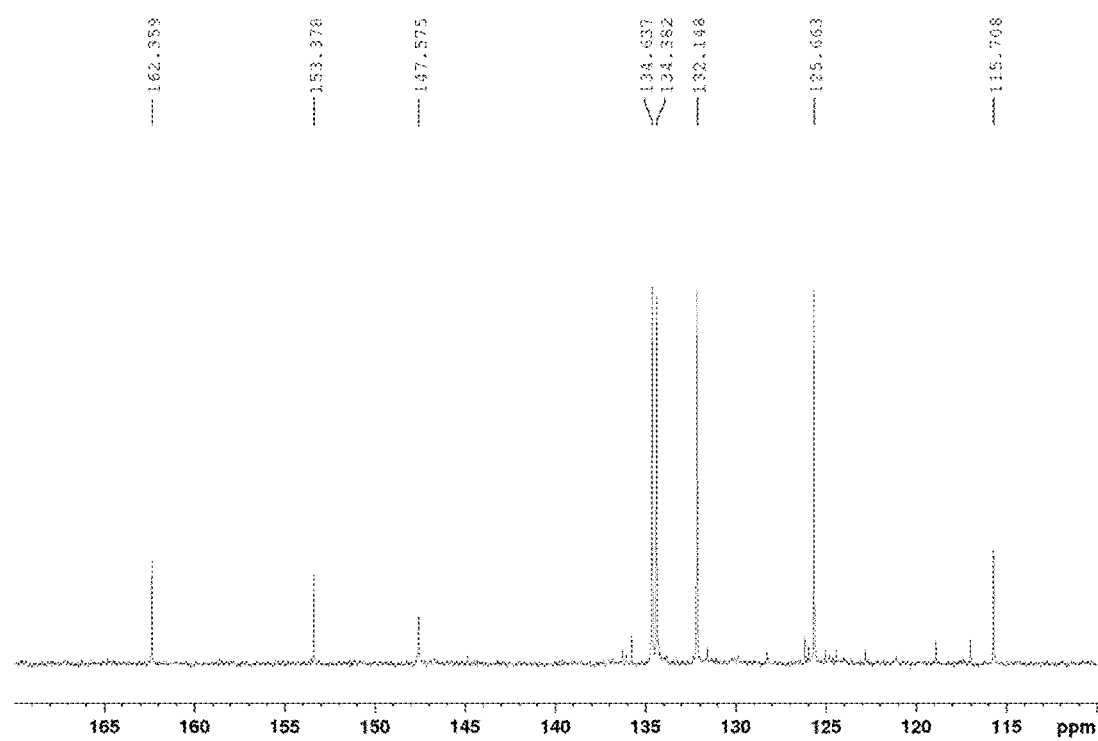
FIG. 25 is the $^{13}$C{$^1$H} NMR (CDCl$_3$, 125 MHz) spectrum for 3-(o-nitrophenyl)-1,4,2-dioxazol-5-one prepared in accordance with an embodiment as described herein.

Compound 11 was confirmed to be 3-(o-nitrophenyl)-1,4,2-dioxazol-5-one. The product was an orange solid with a melting point of 44-46° C. and provided a yield of 0.58 g, 23%. The $^1$H NMR (CDCl$_3$, 500 MHz) spectrum is shown in FIG. 24 and indicates: δ=8.27 (dd, 1H, J=1.9 Hz, 7.0 Hz), 7.85-7.93 (m, 2H), 7.82 (dd, 1H, J=2.3 Hz, 6.7 Hz). The $^{13}$C{$^1$H} NMR (CDCl$_3$, 125 MHz) spectrum is shown in FIG. 25 and indicates: δ=162.4, 153.4, 147.6, 134.6, 134.4, 132.1, 125.7, 115.7.

Figure 26:
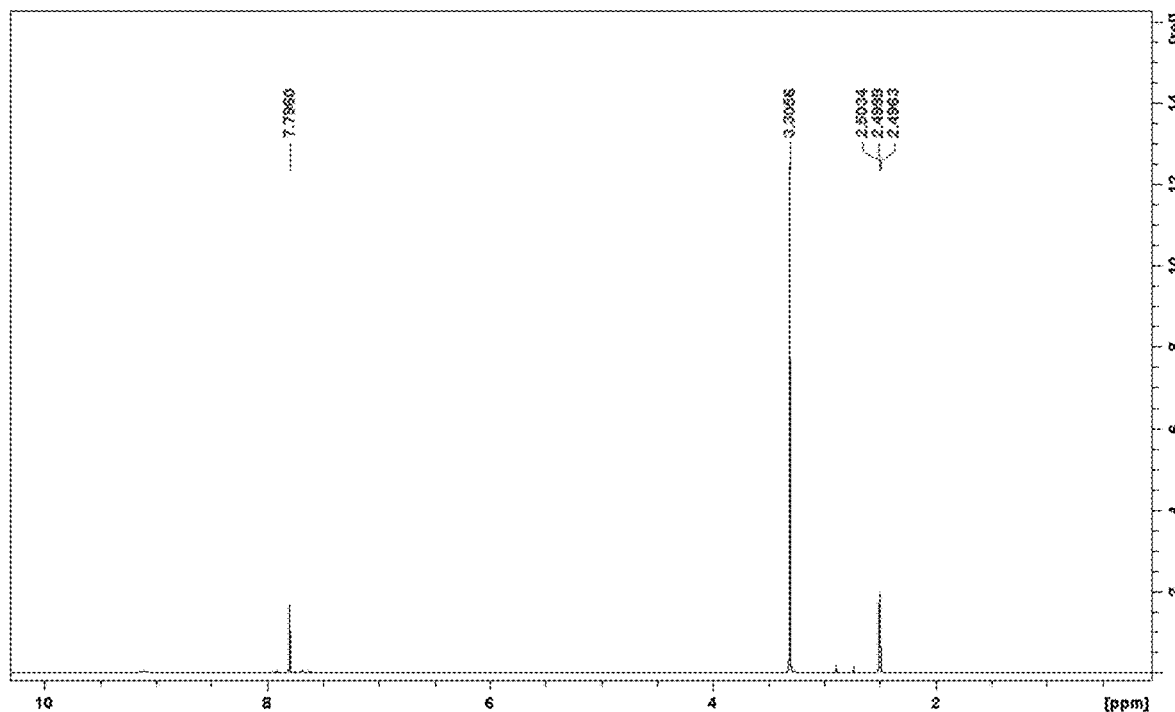
FIG. 26 is the $^1$H NMR (CDCl$_3$, 500 MHz) spectrum for 3,3'-(1,4-phenylene)bis-1,4,2-dioxazol-5-one prepared in accordance with an embodiment as described herein.
Figure 27:
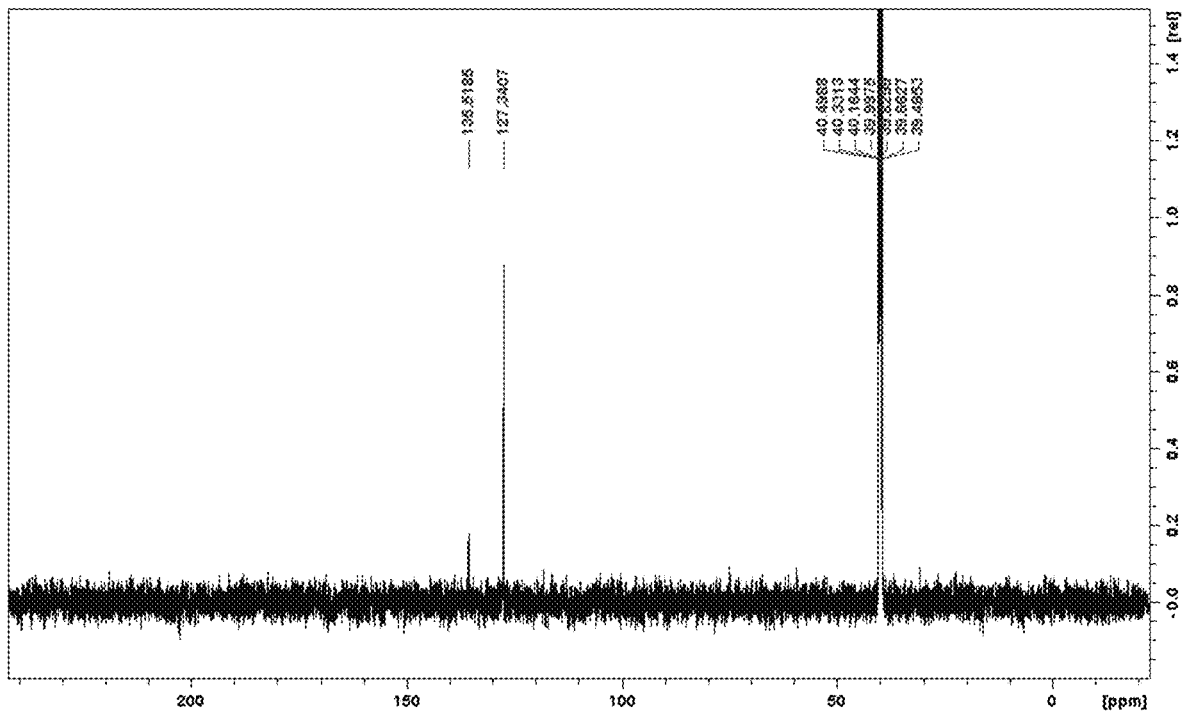
FIG. 27 is the $^{13}C\{^1H\}$ NMR (CDCl$_3$, 125 MHz) spectrum for 3,3'-(1,4-phenylene)bis-1,4,2-dioxazol-5-one prepared in accordance with an embodiment as described herein.

Compound 12 was confirmed to be 3,3'-(1,4-phenylene)bis-1,4,2-dioxazol-5-one. The product was a white solid that decomposed slowly above 180° C. that provided a yield of 2.77 g, 91%. The $^1$H NMR (CDCl$_3$, 500 MHz) spectrum is shown in FIG. 26 and indicates: δ=7.80 (s, 4H). The $^{13}$C{$^1$H} NMR (CDCl$_3$, 125 MHz) spectrum is shown in FIG. 27 and indicates: δ=135.5, 127.3 (it is suspected the weak $^{13}$C intensities are due to sample decomposition).

Figure 28:
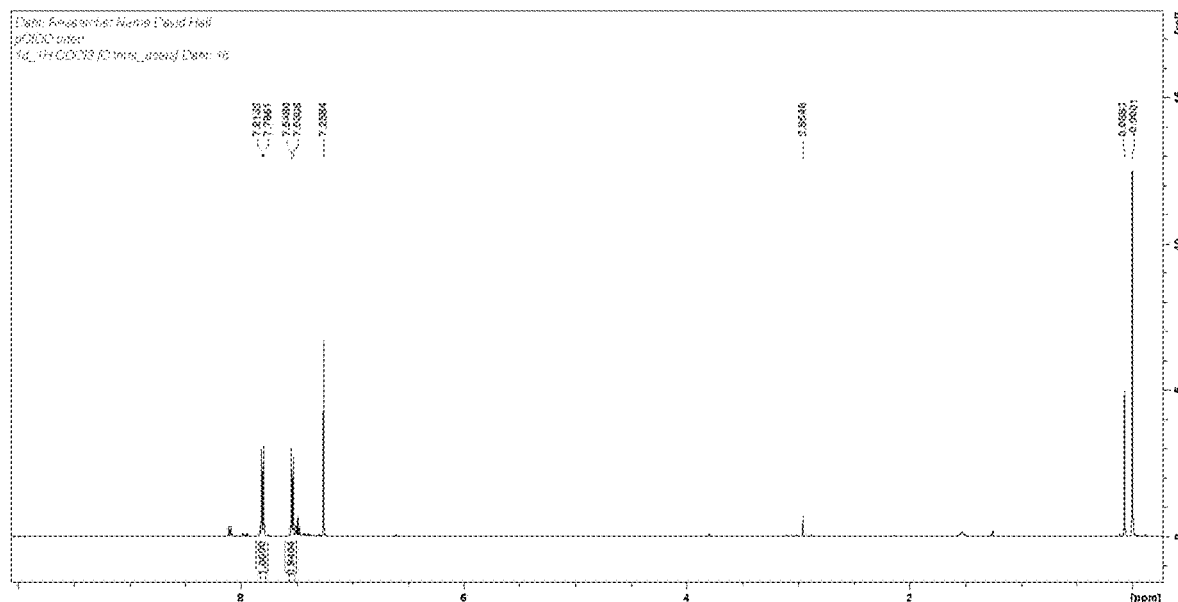
FIG. 28 is the $^1H$ NMR (CDCl$_3$, 500 MHz) spectrum for 3-(p-chlorophenyl)-1,4,2-dioxazol-5-one prepared in accordance with an embodiment as described herein.
Figure 29:
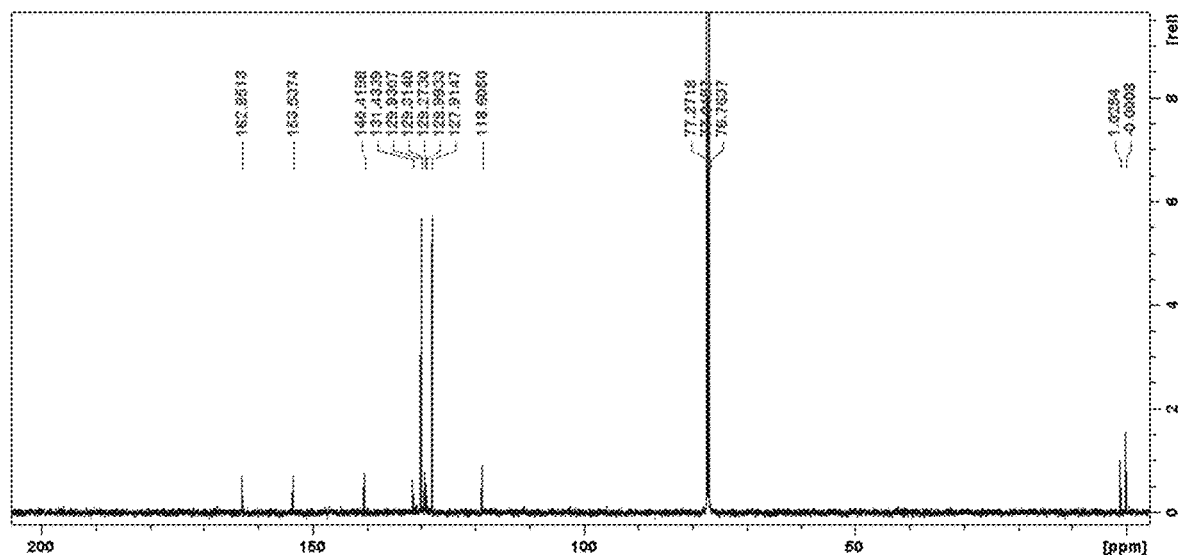
FIG. 29 is the $^{13}C\{^1H\}$ NMR (CDCl$_3$, 125 MHz) spectrum for 3-(p-chlorophenyl)-1,4,2-dioxazol-5-one prepared in accordance with an embodiment as described herein.

Compound 13 was confirmed to be 3-(p-chlorophenyl)-1,4,2-dioxazol-5-one. The product was a white solid that decomposed violently at 145° C. and provided a yield of 1.07 g, 49%. The $^1$H NMR (CDCl$_3$, 500 MHz) spectrum is shown at FIG. 28 and indicates: δ=7.80 (d, 2H, J=8.7 Hz), 7.54 (d, 2H, J=8.6 Hz). The $^{13}$C{$^1$H} NMR (CDCl$_3$, 125 MHz) spectrum is shown at FIG. 29 and indicates: δ=162.9, 153.5, 140.4, 131.4, 129.9, 129.3, 127.9, 118.6.

Figure 30:
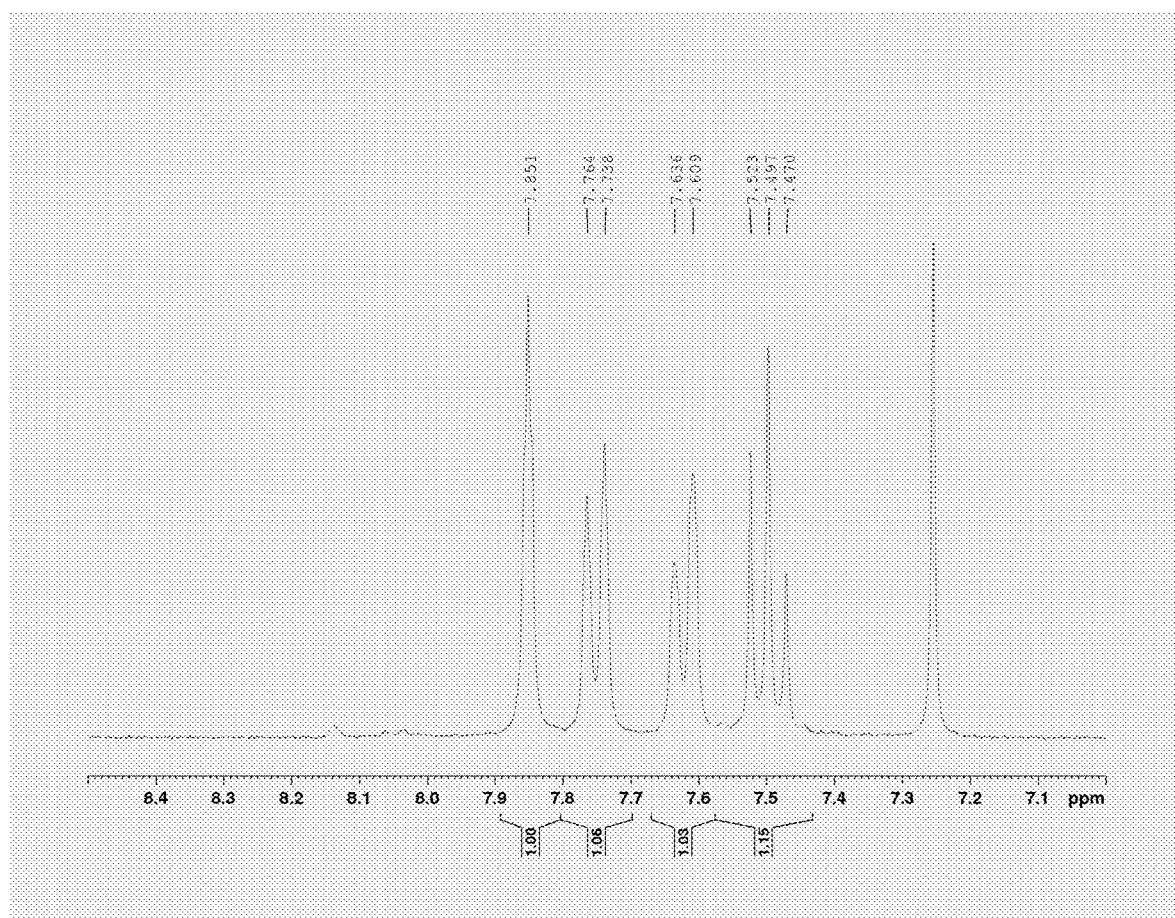
FIG. 30 is the $^1H$ NMR (CDCl$_3$, 300 MHz) spectrum for 3-(m-chlorophenyl)-1,4,2-dioxazol-5-one prepared in accordance with an embodiment as described herein.
Figure 31:
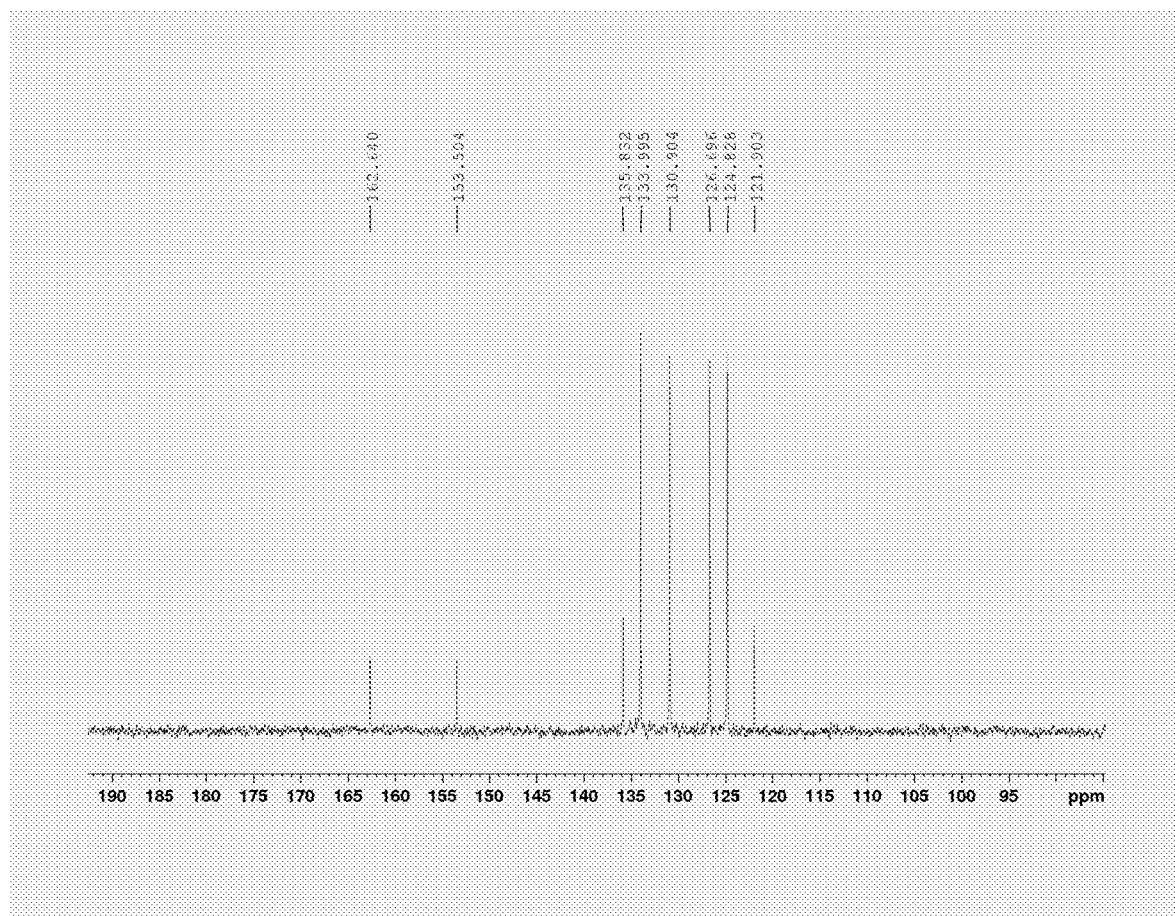
FIG. 31 is the $^{13}C\{^1H\}$ NMR (CDCl$_3$, 125 MHz) spectrum for 3-(m-chlorophenyl)-1,4,2-dioxazol-5-one prepared in accordance with an embodiment as described herein.

Compound 14 was confirmed to be 3-(m-chlorophenyl)-1,4,2-dioxazol-5-one. The product was an off-white solid with a melting point of 34-35° C. and provided a yield of 1.57 g, 66%. The $^1$H NMR (CDCl$_3$, 300 MHz) spectrum is shown at FIG. 30 and indicates: δ=7.85 (br. s, 1H), 7.75 (d, 1H, J=7.8 Hz), 7.62 (d, 1H, J=8.45 Hz), 7.50 (t, 1H, J=7.8 Hz). The $^{13}$C{$^1$H} NMR (CDCl$_3$, 125 MHz) spectrum is shown at FIG. 31 and indicates: δ=162.6, 153.5, 135.8, 134.0, 130.9, 126.7, 124.8, 121.9.

Figure 32:
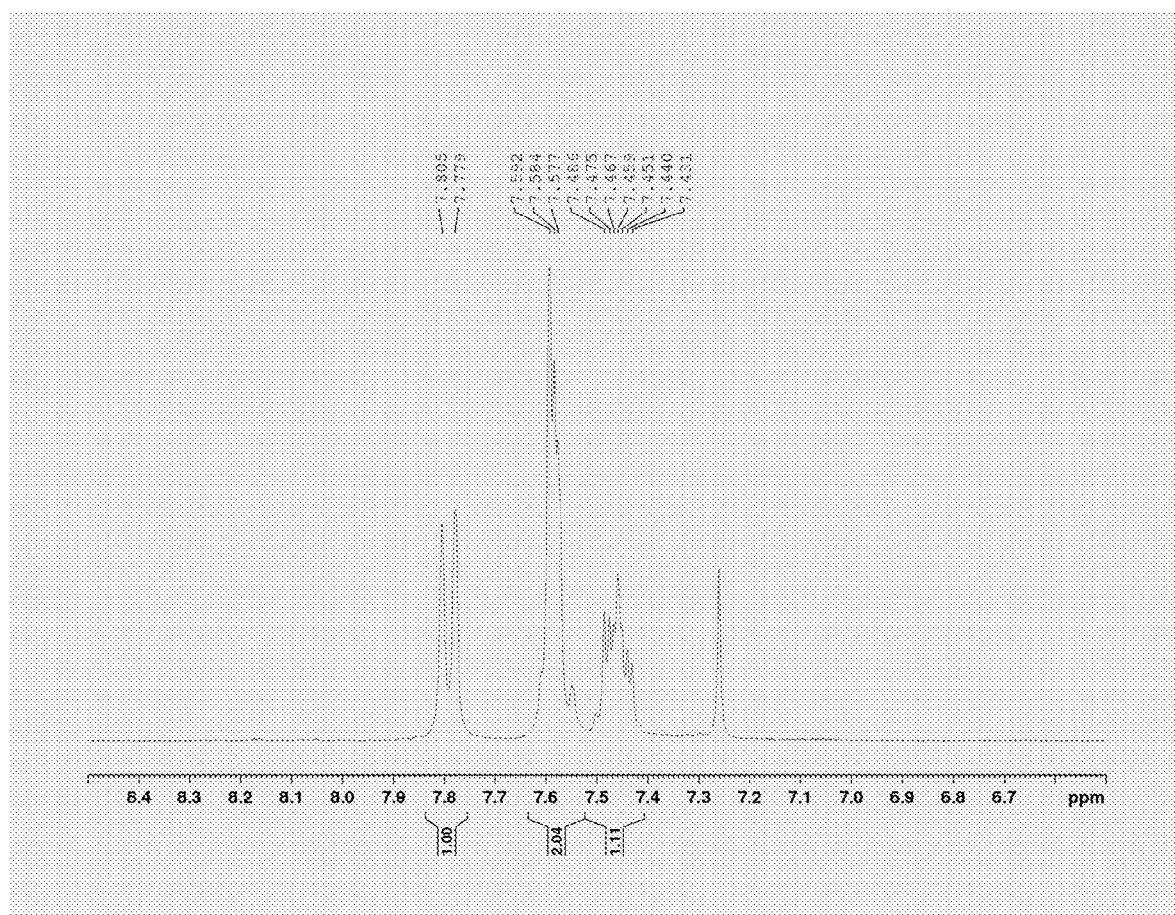
FIG. 32 is the $^1H$ NMR (CDCl$_3$, 300 MHz) spectrum for 3-(o-chlorophenyl)-1,4,2-dioxazol-5-one prepared in accordance with an embodiment as described herein.
Figure 33:
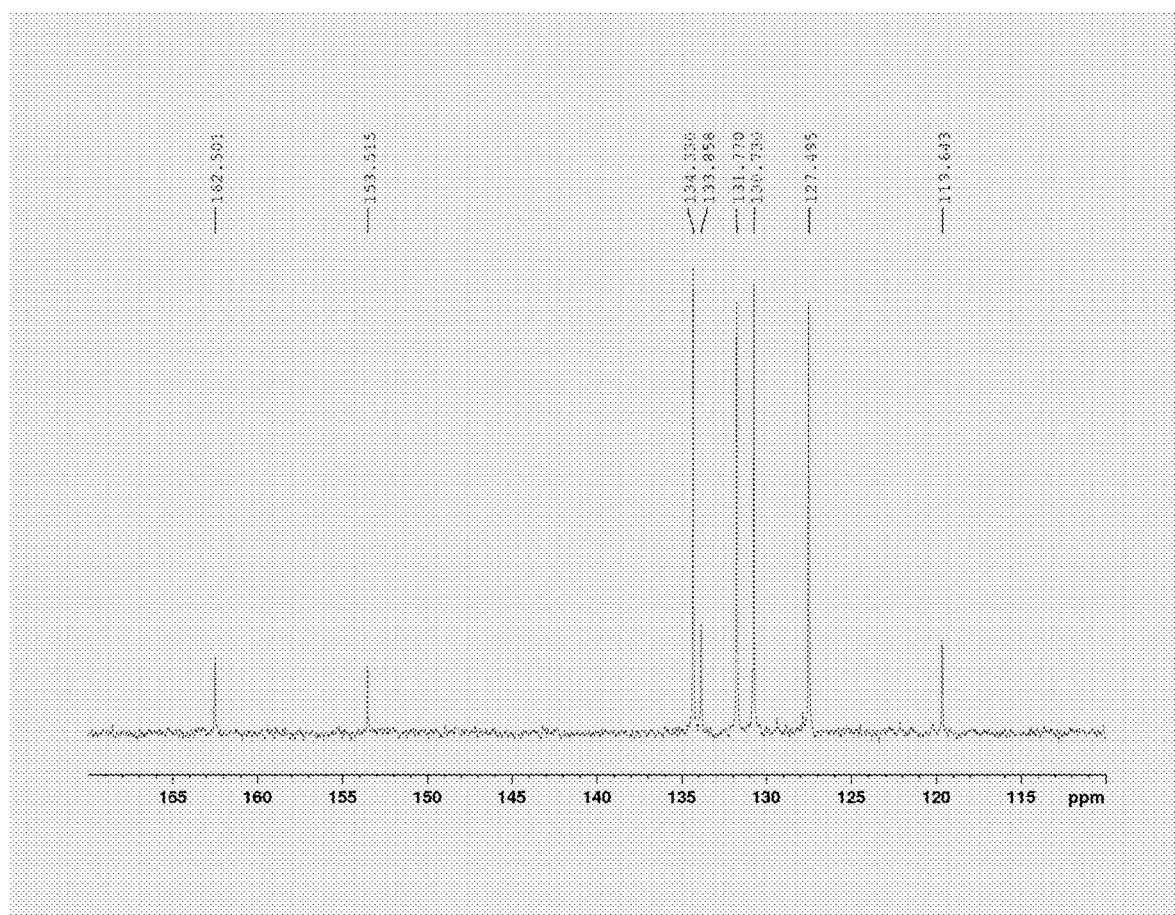
FIG. 33 is the $^{13}C\{^1H\}$ NMR (CDCl$_3$, 125 MHz) spectrum for 3-(o-chlorophenyl)-1,4,2-dioxazol-5-one prepared in accordance with an embodiment as described herein.

Compound 15 was confirmed to be 3-(o-chlorophenyl)-1,4,2-dioxazol-5-one. The product was an off-white solid with a melting point of 41-43° C. and provided a yield of 1.57 g, 58%. The $^1$H NMR (CDCl$_3$, 300 MHz) spectrum is shown at FIG. 32 and indicates: δ=7.78 (d, 1H, J=7.7 Hz), 7.52-7.63 (m, 2H), 7.42-7.50 (m, 1H). The $^{13}$C{$^1$H} NMR (CDCl$_3$, 125 MHz) spectrum is shown at FIG. 33 and indicates: δ=162.5, 153.5, 134.3, 133.9, 131.8, 130.7, 127.5, 119.6.

One-Pot Method—Large Scale

Hydroxylamine hydrochloride (168 mmol, 11.67 g, 1.1 eq), was dissolved in N,N-dimethylformamide (100 mL) at room temperature in a 2000-mL three-necked round-bottomed flask equipped with a magnetic stir bar. Triethylamine (168 mmol, 23.5 mL, 1.1 eq) was added in one portion. The solution was stirred for 5 minutes, then ethyl acetate (1100 mL) was added to the solution, and the reaction mixture was cooled to 0° C.

Benzoyl chloride (153 mmol, 17.8 mL, 1.0 eq) and triethylamine (23.5 mL, 168 mmol, 1.1 eq) were placed into separate dropper funnels, and added dropwise to the 2000 mL round bottomed flask over the course of 15 minutes. The reaction was allowed to gradually warm up to room temperature.

After five hours, N,N'-carbonyldiimidazole (153 mmol, 24.80 g, 1.0 eq) was added to the round-bottomed flask in one portion, and the reaction was allowed to proceed for another 30 minutes at room temperature. The reaction was quenched with 200 mL of 2 M HCl$_{(aq)}$, extracted with ethyl acetate (2×200 mL), and dried over anhydrous Na$_2$SO$_4$. The ethyl acetate was evaporated under reduced pressure, and 10% aqueous NaHCO$_3$ was added to the remaining liquid to give the product 3-phenyl-1,4,2-dioxazol-5-one (20.3 g, 81%), which was collected by suction filtration.

Attenuated Total Reflectance Fourier Transform Infrared (ATR-FTIR) Spectroscopy

Figure 34:
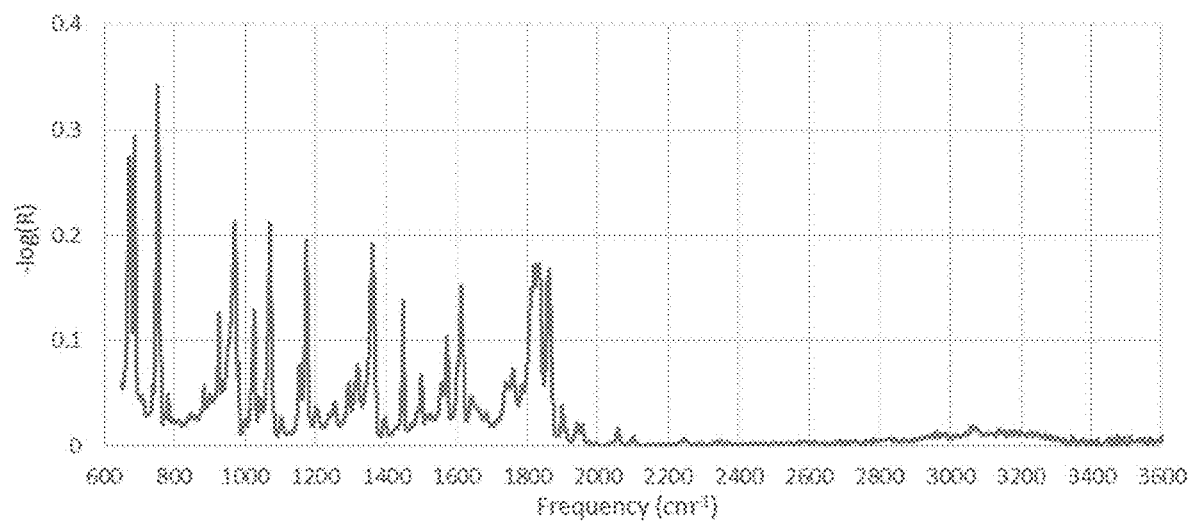
FIG. 34 is the ATR-FTIR spectrum for 3-phenyl-1,4,2-dioxazol-5-one prepared in accordance with an embodiment as described herein.

Products from the testing scale experiment were characterized by Fourier transform infrared spectroscopy (FTIR) using a Cary 630 FTIR (Agilent Technologies) equipped with a germanium crystal attenuated total reflectance (ATR) accessory, controlled by MicroLab PC software, and measured at 4 cm$^{-1}$ resolution. The results of the ATR-FTIR for 3-phenyl-1,4,2-dioxazol-5-one is shown in FIG. 34.

Figure 35:
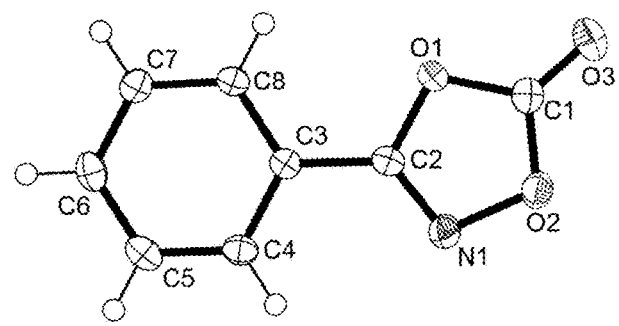
FIG. 35 shows the molecular structure of 3-phenyl-1,4,2-dioxazol-5-one (1), determined by single crystal X-ray diffraction (H atoms added based on $^1H$ and $^{13}C$ NMR results) prepared in accordance with an embodiment as described herein.

X-Ray Data Collection, Reduction, Solution and Refinement 3-phenyl-1,4,2-dioxazol-5-one crystals, obtained in the above described testing scale experiment, were attached to the tip of a 150 μm MicroLoop with paratone-N oil. Measurements were made on a Bruker APEXII CCD equipped diffractometer (30 mA, 50 KV) using monochromated Mo Kα radiation (λ=0.71073 Å) at 125 K. APEX3 software1 was used for the initial orientation and unit cell were indexed using a least-squares analysis of a random set of reflections collected from three series of 0.5° wide scans, 10 seconds per frame and 12 frames per series that were well distributed in reciprocal space. For data collection, four ω-scan frame series were collected with 0.5° wide scans, 30 second frames and 366 frames per series at varying φ angles (φ=0°, 90°, 180°, 270°). The crystal to detector distance was set to 6 cm and a complete sphere of data was collected. Cell refinement and data reduction were performed with the Bruker APEX3 software[1], which corrects for beam inhomogeneity, possible crystal decay, Lorentz and polarization effects. Data processing and a multi-scan absorption correction was applied using APEX3 software package. The structure was solved using SHELXT and all non-hydrogen atoms were refined anisotropically using SHELXL with the OLEX2 graphical user interface. Hydrogen atoms were placed in calculated positions using an appropriate riding model and coupled isotropic temperature factors. Figures were made using Ortep-3 for Windows. FIG. 35 shows the molecular structure of 3-phenyl-1,4,2-dioxazol-5-one (1), determined by single crystal X-ray diffraction (H atoms added based on $^1$H and $^{13}$C NMR results). Additional data are shown in Tables 3-7.

TABLE 3

Crystal data and structure refinement for 3-phenyl-1,4,2-dioxazol-5-one ("PDO")

| | |
|---|---|
| Empirical formula | C8 H5 N O3 |
| Formula weight | 163.13 |
| Temperature | 421.15 K |

TABLE 3-continued

Crystal data and structure refinement for 3-phenyl-1,4,2-dioxazol-5-one ("PDO")

| | |
|---|---|
| Wavelength | 0.71073 Å |
| Crystal system | Monoclinic |
| Space group | P 1 21/n 1 |
| Unit cell dimensions | a = 8.0463(11) Å α = 90°. |
| | b = 5.4847(8) Å β = 93.785(2)°. |
| | c = 16.073(2) Å γ = 90°. |
| Volume | 707.78(17) Å$^3$ |
| Z | 4 |
| Density (calculated) | 1.531 Mg/m$^3$ |
| Absorption coefficient | 0.120 mm$^{-1}$ |
| F(000) | 336 |
| Crystal size | 0.17 × 0.16 × 0.05 mm$^3$ |
| Theta range for data collection | 2.540 to 29.209°. |
| Index ranges | −10 <= h <= 10, −7 <= k <= 7, |
| | −21 <= l <= 21 |
| Reflections collected | 8513 |
| Independent reflections | 1825 [R(int) = 0.0215] |
| Completeness to theta = 25.242° | 100.0% |
| Absorption correction | Semi-empirical from equivalents |
| Max. and min. transmission | 0.7458 and 0.7062 |
| Refinement method | Full-matrix least-squares on F$^2$ |
| Data/restraints/parameters | 1825/0/109 |
| Goodness-of-fit on F$^2$ | 1.030 |
| Final R indices [I > 2sigma(I)] | R1 = 0.0329, wR2 = 0.0796 |
| R indices (all data) | R1 = 0.0425, wR2 = 0.0862 |
| Extinction coefficient | n/a |
| Largest diff. peak and hole | 0.255 and −0.218 e · Å$^{-3}$ |

TABLE 4

Atomic coordinates (×10$^4$) and equivalent isotropic displacement parameters (Å$^2$ × 10$^3$) for PDO. U(eq) is defined as one third of the trace of the orthogonalized U$^{ij}$ tensor.

| | x | y | z | U(eq) |
|---|---|---|---|---|
| C(1) | 4035(1) | 5753(2) | 2698(1) | 23(1) |
| N(1) | 4320(1) | 8141(2) | 3847(1) | 25(1) |
| O(1) | 3273(1) | 4658(1) | 3336(1) | 21(1) |
| C(2) | 3510(1) | 6197(2) | 4003(1) | 19(1) |
| O(2) | 4670(1) | 7894(2) | 2986(1) | 27(1) |
| C(3) | 2852(1) | 5520(2) | 4794(1) | 18(1) |
| O(3) | 4122(1) | 4934(2) | 2020(1) | 32(1) |
| C(4) | 3109(1) | 7085(2) | 5478(1) | 22(1) |
| C(5) | 2443(1) | 6490(2) | 6224(1) | 26(1) |
| C(6) | 1542(1) | 4354(2) | 6294(1) | 25(1) |
| C(7) | 1311(1) | 2785(2) | 5620(1) | 22(1) |
| C(8) | 1965(1) | 3353(2) | 4866(1) | 20(1) |

TABLE 5

Bond lengths [Å] and angles [°] for PDO.

| | |
|---|---|
| C(1)—O(1) | 1.3679(13) |
| C(1)—O(2) | 1.3496(14) |
| C(1)—O(3) | 1.1865(14) |
| N(1)—C(2) | 1.2825(14) |
| N(1)—O(2) | 1.4372(12) |
| O(1)—C(2) | 1.3670(12) |
| C(2)—C(3) | 1.4582(15) |
| C(3)—C(4) | 1.3991(15) |
| C(3)—C(8) | 1.3951(15) |
| C(4)—H(4) | 0.9300 |
| C(4)—C(5) | 1.3842(16) |
| C(5)—H(5) | 0.9300 |
| C(5)—C(6) | 1.3862(17) |
| C(6)—H(6) | 0.9300 |
| C(6)—C(7) | 1.3874(16) |
| C(7)—H(7) | 0.9300 |
| C(7)—C(8) | 1.3872(15) |
| C(8)—H(8) | 0.9300 |
| O( )—C(1)—O(1) | 107.68(9) |

TABLE 5-continued

Bond lengths [Å] and angles [°] for PDO.

| | |
|---|---|
| O(3)—C(1)—O(1) | 125.43(11) |
| O(3)—C(1)—O(2) | 126.89(11) |
| C(2)—N(1)—O(2) | 104.08(9) |
| C(2)—O(1)—C(1) | 105.63(9) |
| N(1)—C(2)—O(1) | 114.05(9) |
| N(1)—C(2)—C(3) | 126.87(10) |
| O(1)—C(2)—C(3) | 119.08(9) |
| C(1)—O(2)—N(1) | 108.54(8) |
| C(4)—C(3)—C(2) | 119.05(10) |
| C(8)—C(3)—C(2) | 120.45(9) |
| C(8)—C(3)—C(4) | 120.49(10) |
| C(3)—C(4)—H(4) | 120.3 |
| C(5)—C(4)—C(3) | 119.34(11) |
| C(5)—C(4)—H(4) | 120.3 |
| C(4)—C(5)—H(5) | 119.8 |
| C(4)—C(5)—C(6) | 120.32(11) |
| C(6)—C(5)—H(5) | 119.8 |
| C(5)—C(6)—H(6) | 119.9 |
| C(5)—C(6)—C(7) | 120.25(11) |
| C(7)—C(6)—H(6) | 119.9 |
| C(6)—C(7)—H(7) | 119.9 |
| C(8)—C(7)—C(6) | 120.29(10) |
| C(8)—C(7)—H(7) | 119.9 |
| C(3)—C(8)—H(8) | 120.4 |
| C(7)—C(8)—C(3) | 119.29(10) |
| C(7)—C(8)—H(8) | 120.4 |

Symmetry transformations used to generate equivalent atoms:

TABLE 6

Anisotropic displacement parameters (Å$^2$ × 10$^3$) for PDO. The anisotropic displacement factor exponent takes the form: $-2\pi^2[h^2 a^{*2} U^{11} + \ldots + 2 h k a^* b^* U^{12}]$

| | U$^{11}$ | U$^{22}$ | U$^{33}$ | U$^{23}$ | U$^{13}$ | U$^{12}$ |
|---|---|---|---|---|---|---|
| C(1) | 20(1) | 26(1) | 22(1) | 3(1) | 1(1) | 3(1) |
| N(1) | 27(1) | 26(1) | 20(1) | 2(1) | 0(1) | −4(1) |
| O(1) | 24(1) | 22(1) | 18(1) | −1(1) | 2(1) | −1(1) |
| C(2) | 17(1) | 19(1) | 19(1) | −1(1) | −2(1) | 2(1) |
| O(2) | 28(1) | 30(1) | 23(1) | 4(1) | 2(1) | −5(1) |
| C(3) | 16(1) | 18(1) | 19(1) | 0(1) | −1(1) | 4(1) |
| O(3) | 35(1) | 38(1) | 22(1) | −1(1) | 6(1) | 5(1) |
| C(4) | 21(1) | 20(1) | 24(1) | −2(1) | −1(1) | 2(1) |
| C(5) | 27(1) | 28(1) | 21(1) | −5(1) | −2(1) | 6(1) |
| C(6) | 24(1) | 30(1) | 20(1) | 3(1) | 3(1) | 7(1) |
| C(7) | 21(1) | 21(1) | 26(1) | 3(1) | 2(1) | 2(1) |
| C(8) | 20(1) | 19(1) | 20(1) | −1(1) | −1(1) | 2(1) |

TABLE 7

Hydrogen coordinates (×10$^4$) and isotropic displacement parameters (Å$^2$ × 10$^3$) for PDO.

| | x | y | z | U(eq) |
|---|---|---|---|---|
| H(4) | 3722 | 8511 | 5432 | 26 |
| H(5) | 2600 | 7529 | 6680 | 31 |
| H(6) | 1092 | 3970 | 6796 | 30 |
| H(7) | 715 | 1347 | 5672 | 27 |
| H(8) | 1814 | 2299 | 4414 | 23 |

Mass Spectrometry

Figure 36:
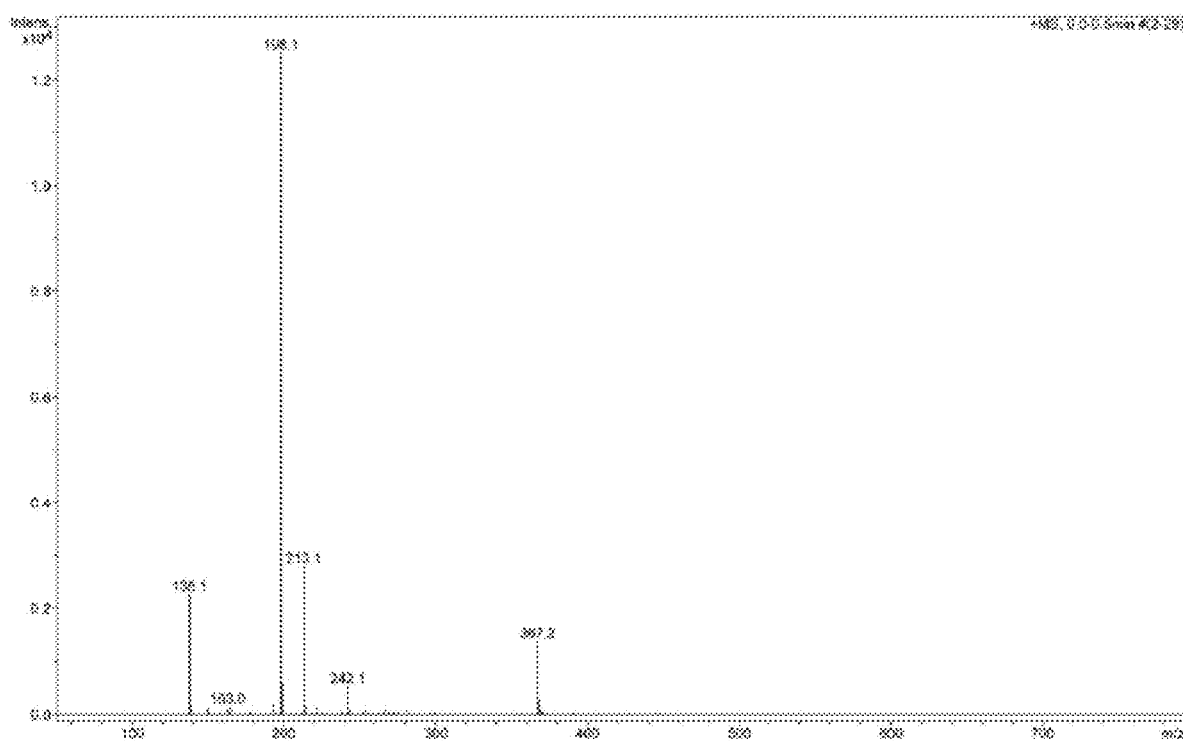
FIG. 36 is the mass spectrum for 3-phenyl-1,4,2-dioxazol-5-one prepared in accordance with an embodiment as described herein.

Mass Spectrometry was then performed on the resulting PDO product of the testing scale scale experiment, which had an exact mass of 163.027 u. The resulting mass spectrum is shown in FIG. 36. The data was collected with a CEC 21-110B Mass Spectrometer operated at low resolution (m/z=10-800, M/ΔM=2500) in positive ion mode using soft EI ionization. PDO and related compounds showed very poor or no signal intensity, preventing collecting of high resolution spectrum. The main peak at 198.1 amu is thought to be an impurity produced by oxidation/decomposition of the PDO molecule (for example, this peak may correspond to $C_8H_8O_5N^+$ (m/z=198.04 amu) or a similar compound).

As described herein, provided is a simple one-pot method for the synthesis of 3-aryl-substituted-1,4,2-dioxazol-5-ones. The reaction conditions are mild and can easily be performed in a single day with minimal energy requirements. Moreover, the methods described herein do not require the use of toxic halogenated solvents. Although N,N-dimethylformamide is also considered a harmful solvent, the present methods primarily use ethyl acetate, which is a relatively benign solvent. Therefore only a very small amount of N,N-dimethylformamide is needed, relative to the quantity of dichloromethane required for existing procedures. In addition, the reaction is robust, shown herein tolerate a wide variety of substituents on the aromatic ring. The precursor materials are significantly more available from commercial suppliers than previously known methods. Finally, the reaction is demonstrably easy to scale up, making it a potentially suitable route for industrial scale production of 3-aryl-1,4,2-dioxazol-5-one compounds. It is noted that some benzoic acid impurities were present in the product, but these were readily removed by washing with aqueous $Na_2CO_3$ solution. In certain embodiments described herein, the product should not be washed with stronger bases, such as NaOH, which could cause the product to hydrolyze.

The foregoing disclosure is not intended to limit the present disclosure to the precise forms or particular fields of use disclosed. As such, it is contemplated that various alternative embodiments and/or modifications to the present disclosure, whether explicitly described or implied herein, are possible in light of the disclosure. Having thus described embodiments of the present disclosure, a person of ordinary skill in the art will recognize that changes may be made in form and detail without departing from the scope of the present disclosure. Thus, the present disclosure is limited only by the claims. Reference to additives in the specification are generally to operative additives unless otherwise noted in the specification.

In the foregoing specification, the disclosure has been described with reference to specific embodiments. However, as one skilled in the art will appreciate, various embodiments disclosed herein can be modified or otherwise implemented in various other ways without departing from the spirit and scope of the disclosure. Accordingly, this description is to be considered as illustrative and is for the purpose of teaching those skilled in the art the manner of making and using various embodiments of the disclosed chemical system. It is to be understood that the forms of disclosure herein shown and described are to be taken as representative embodiments. Equivalent elements, or materials may be substituted for those representatively illustrated and described herein. Moreover, certain features of the disclosure may be utilized independently of the use of other features, all as would be apparent to one skilled in the art after having the benefit of this description of the disclosure. Expressions such as "including", "comprising", "incorporating", "consisting of", "have", "is" used to describe and claim the present disclosure are intended to be construed in a non-exclusive manner, namely allowing for items, components or elements not explicitly described also to be present. Reference to the singular is also to be construed to relate to the plural. Reference to "about" or "approximately" is to be construed to mean plus or minus 10%.

Further, various embodiments disclosed herein are to be taken in the illustrative and explanatory sense, and should in no way be construed as limiting of the present disclosure. All joinder references (e.g., attached, affixed, coupled, connected, and the like) are only used to aid the reader's understanding of the present disclosure, and may not create limitations, particularly as to the position, orientation, or use of the systems and/or methods disclosed herein. Therefore, joinder references, if any, are to be construed broadly. Moreover, such joinder references do not necessarily infer that two elements are directly connected to each other.

Additionally, all numerical terms, such as, but not limited to, "first", "second", "third", "primary", "secondary", "main" or any other ordinary and/or numerical terms, should also be taken only as identifiers, to assist the reader's understanding of the various elements, embodiments, variations and/or modifications of the present disclosure, and may not create any limitations, particularly as to the order, or preference, of any element, embodiment, variation and/or modification relative to, or over, another element, embodiment, variation and/or modification.

It will also be appreciated that one or more of the elements depicted in the drawings/figures can also be implemented in a more separated or integrated manner, or even removed or rendered as inoperable in certain cases, as is useful in accordance with a particular application.

What is claimed is:

1. A method of preparing a 3-R-1,4,2-dioxazol-5-one compound, comprising:
    providing a first reaction mixture comprising hydroxylamine hydrochloride, triethylamine, and a first organic solvent;
    providing a second reaction mixture comprising an R-substituted acyl chloride;
    providing a third reaction mixture comprising triethylamine;
    combining the first, second and third reaction mixtures to form a fourth reaction mixture;
    adding N,N'-carbonyldiimidazole to the fourth reaction mixture to form a fifth reaction mixture; and
    obtaining a 3-R-1,4,2-dioxazol-5-one compound from the fifth reaction mixture, wherein the method is performed by a one-pot method.

2. The method of claim 1, wherein the R-substituted acyl chloride is selected from the group consisting of benzoyl chloride, 2-thiophenecarbonyl chloride, p-toluoyl chloride, 2-naphthoyl chloride, p fluorobenzoyl chloride, m-fluorobenzoyl chloride, o-fluorobenzoyl chloride, p methoxybenzoyl chloride, p-nitrobenzoyl chloride, m-nitrobenzoyl chloride, o-nitrobenzoyl chloride, p-teraphthaloyl chloride, p-chlorobenzoyl chloride, m-chlorobenzoyl chloride, o chlorobenzoyl chloride, and combinations thereof.

3. The method of claim 1, wherein the first organic solvent is N,N-dimethylformamide (DMF).

4. The method of claim 1, further comprising dissolving the R-substituted acyl chloride in a second organic solvent to form the second reaction mixture.

5. The method of claim 4, wherein the second organic solvent is selected from the group consisting of ethyl acetate and tetrahydrofuran.

6. The method of claim 1, wherein the 3-R-1,4,2-dioxazol-5-one compound is obtained at a purity of at least 50 wt. %.

7. The method of claim 1, further comprising purifying the 3-R-1,4,2-dioxazol-5-one compound to a purity of at least 75 wt. %.

8. The method of claim 7, further comprising purifying the 3-R-1,4,2-dioxazol-5-one compound to a purity of at least 90 wt. %.

9. The method of claim 1, wherein the method is performed at ambient temperature and pressure.

10. The method of claim 1, wherein the first reaction mixture is cooled to 0° C.

11. The method of claim 1, wherein the 3-R-1,4,2-dioxazol-5-one compound is selected from the group consisting of 3-phenyl-1,4,2-dioxazol-5-one, 3-thiophene-1,4,2-dioxazol-5-one, 3-tolyl-1,4,2-dioxazol-5-one, 3-(2-naphthyl)-1,4,2-dioxazol-5-one, 3-(p-fluorophenyl)-1,4,2-dioxazol-5-one, 3-(m-fluorophenyl)-1,4,2-dioxazol-5-one, 3-(o-fluorophenyl)-1,4,2-dioxazol-5-one, 3-(p-methoxyphenyl)-1,4,2-dioxazol-5-one, 3-(p-nitrophenyl)-1,4,2-dioxazol-5-one, 3-(m-nitrophenyl)-1,4,2-dioxazol-5-one, 3-(o-nitrophenyl)-1,4,2-dioxazol-5-one, 3,3'-(1,4-phenylene)-bis-1,4,2-dioxazol-5-one, 3-(p-chlorophenyl)-1,4,2-dioxazol-5-one, 3-(m-chlorophenyl)-1,4,2-dioxazol-5-one, 3-(o-chlorophenyl)-1,4,2-dioxazol-5-one, and combinations thereof.

12. The method of claim 1, further comprising dissolving the triethylamine in a third organic solvent to form the third reaction mixture.

13. The method of claim 7, wherein the third organic solvent is selected from the group consisting of ethyl acetate, tetrahydrofuran, and combinations thereof.

14. The method of claim 1, further comprising adding an acid to the fifth reaction mixture prior to obtaining the 3-R-1,4,2-dioxazol-5-one compound.

15. A method of preparing a 3-R-1,4,2-dioxazol-5-one compound, comprising:
    combining hydroxylamine hydrochloride, triethylamine, N,N-dimethylformamide (DMF) and ethyl acetate to form a first reaction mixture, wherein the first reaction mixture is cooled to 0° C.;
    adding an R-substituted acyl chloride and additional triethylamine to the first reaction mixture to form a second reaction mixture, wherein the second reaction mixture is warmed to room temperature;
    adding N,N'-carbonyldiimidazole to the second reaction mixture to form a third reaction mixture;
    adding an acid to the third reaction mixture to form a quenched reaction mixture; and
    obtaining a 3-R-1,4,2-dioxazol-5-one compound from the quenched reaction mixture, wherein the method is performed by a one-pot method.

* * * * *